(12) United States Patent  (10) Patent No.: US 7,798,998 B2
Thompson et al.  (45) Date of Patent: Sep. 21, 2010

(54) ELASTICALLY DEFORMABLE SURGICAL ACCESS DEVICE

(75) Inventors: Ronald J. Thompson, Ft. Thomas, KY (US); Dominick Mastri, Bridgeport, CT (US); Kurt Azarbarzin, Fairfield, CT (US); Jack B. Stubbs, Waynesville, OH (US)

(73) Assignee: SurgiQuest, Inc., Orange, CT (US)

( * ) Notice: Subject to any disclaimer, the term of this patent is extended or adjusted under 35 U.S.C. 154(b) by 831 days.

(21) Appl. No.: 11/544,856

(22) Filed: Oct. 6, 2006

(65) Prior Publication Data
US 2008/0086167 A1  Apr. 10, 2008

(51) Int. Cl.
*A61M 5/178* (2006.01)
(52) U.S. Cl. .................................. 604/164.04
(58) Field of Classification Search ........... 600/184, 600/201, 203, 208, 213; 604/104, 164.13; 606/108, 198
See application file for complete search history.

(56) References Cited

U.S. PATENT DOCUMENTS

| | | | |
|---|---|---|---|
| 2,691,985 A * | 10/1954 | Newsom | 606/196 |
| 3,721,229 A | 3/1973 | Panzer | |
| 4,607,619 A | 8/1986 | Seike et al. | |
| 4,655,752 A | 4/1987 | Honkanen et al. | |
| 4,676,782 A | 6/1987 | Yamamoto et al. | |
| 4,929,235 A | 5/1990 | Merry et al. | |
| 4,944,732 A * | 7/1990 | Russo | 604/247 |
| 4,995,868 A | 2/1991 | Brazier | |
| 5,114,407 A | 5/1992 | Burbank | |
| 5,122,122 A | 6/1992 | Allgood | |
| 5,125,897 A * | 6/1992 | Quinn et al. | 604/99.03 |
| 5,147,316 A | 9/1992 | Castillenti | |
| 5,183,464 A | 2/1993 | Dubrul et al. | |

(Continued)

FOREIGN PATENT DOCUMENTS

DE    26 11 107 A1    9/1977

(Continued)

OTHER PUBLICATIONS

International Search Report for PCT/US2008/060163 dated Oct. 24, 2008.

(Continued)

*Primary Examiner*—Kevin T Truong
(74) *Attorney, Agent, or Firm*—Scott D. Wofsy; Edwards Angell Palmer & Dodge LLP

(57) ABSTRACT

A surgical access device is provided having a surgical access port. The surgical access port has an elongated body with opposed proximal and distal end portions, and defines a longitudinal axis. The body has a central lumen extending therethrough and includes a resilient bulb portion formed between the proximal and distal end portions of the body. The resilient bulb portion is adapted and configured to transition, through engagement with an insertion device, between a first condition in which the bulb portion has a first diameter and a first length and a second condition in which the bulb portion has a second diameter and a second length for insertion and removal through a patient's abdominal wall, and to be retained in place therethrough. The second diameter is less than the first diameter, and the second length is greater than the first length.

41 Claims, 17 Drawing Sheets

U.S. PATENT DOCUMENTS

| | | | |
|---|---|---|---|
| 5,242,412 A | | 9/1993 | Blake, III |
| 5,248,302 A | * | 9/1993 | Patrick et al. .............. 604/178 |
| 5,250,025 A | | 10/1993 | Sosnowski et al. |
| 5,257,973 A | | 11/1993 | Villasuso |
| 5,290,249 A | | 3/1994 | Foster et al. |
| 5,300,035 A | | 4/1994 | Clement |
| 5,330,437 A | | 7/1994 | Durman |
| 5,336,203 A | * | 8/1994 | Goldhardt et al. .......... 604/247 |
| 5,339,803 A | * | 8/1994 | Mayzels et al. ............ 600/201 |
| 5,356,421 A | | 10/1994 | Castro |
| 5,366,445 A | | 11/1994 | Haber et al. |
| 5,366,478 A | | 11/1994 | Brinkerhoff et al. |
| 5,383,861 A | | 1/1995 | Hempel et al. |
| 5,423,770 A | | 6/1995 | Yoon |
| 5,423,777 A | * | 6/1995 | Tajiri et al. ................. 604/294 |
| 5,431,676 A | | 7/1995 | Dubrul et al. |
| 5,441,041 A | | 8/1995 | Sauer et al. |
| 5,445,615 A | | 8/1995 | Yoon |
| 5,454,790 A | | 10/1995 | Dubrul |
| 5,456,284 A | | 10/1995 | Ryan et al. |
| 5,460,170 A | | 10/1995 | Hammerslag |
| 5,472,429 A | | 12/1995 | Yoon |
| 5,490,843 A | | 2/1996 | Hildwein et al. |
| 5,524,644 A | | 6/1996 | Crook |
| 5,545,179 A | | 8/1996 | Williamson, IV |
| D373,418 S | * | 9/1996 | Szpak ........................ D24/112 |
| 5,634,937 A | | 6/1997 | Mollenauer et al. |
| 5,657,097 A | | 8/1997 | Schultz et al. |
| 5,685,820 A | | 11/1997 | Riek et al. |
| 5,697,913 A | | 12/1997 | Sierocuk et al. |
| 5,702,370 A | | 12/1997 | Sylvanowicz et al. |
| 5,707,362 A | | 1/1998 | Yoon |
| 5,725,504 A | | 3/1998 | Collins |
| 5,727,770 A | | 3/1998 | Dennis |
| 5,782,813 A | | 7/1998 | Yoon |
| 5,817,062 A | | 10/1998 | Flom et al. |
| 5,830,191 A | | 11/1998 | Hildwein et al. |
| 5,868,139 A | * | 2/1999 | Zeece, Sr. ................... 128/864 |
| 5,895,377 A | | 4/1999 | Smith et al. |
| 5,906,595 A | | 5/1999 | Powell et al. |
| 5,935,107 A | | 8/1999 | Taylor et al. |
| 5,980,549 A | | 11/1999 | Chin |
| 6,077,288 A | | 6/2000 | Shimomura et al. |
| 6,123,689 A | | 9/2000 | To et al. |
| 6,142,981 A | | 11/2000 | Heck et al. |
| 6,206,823 B1 | | 3/2001 | Kolata et al. |
| 6,228,059 B1 | | 5/2001 | Astarita |
| 6,258,065 B1 | | 7/2001 | Dennis et al. |
| 6,364,892 B1 | | 4/2002 | Jervis |
| 6,432,085 B1 | | 8/2002 | Stellon et al. |
| 6,524,238 B2 | | 2/2003 | Velikaris et al. |
| 6,656,198 B2 | | 12/2003 | Tsonton et al. |
| 6,669,674 B1 | | 12/2003 | Macoviak et al. |
| 6,669,709 B1 | | 12/2003 | Cohn et al. |
| 6,814,715 B2 | | 11/2004 | Bonutti et al. |
| 6,837,891 B2 | | 1/2005 | Davison et al. |
| 6,860,869 B2 | | 3/2005 | Dennis |
| 6,972,026 B1 | | 12/2005 | Caldwell et al. |
| 7,052,454 B2 | | 5/2006 | Taylor |
| 7,056,303 B2 | | 6/2006 | Dennis et al. |
| 7,056,329 B2 | | 6/2006 | Kerr |
| 7,388,466 B2 | * | 6/2008 | Ghabra et al. ............... 340/5.61 |
| 7,473,243 B2 | | 1/2009 | Dennis et al. |
| 7,625,361 B2 | * | 12/2009 | Suzuki et al. ............... 604/264 |
| 2003/0093104 A1 | | 5/2003 | Bonner et al. |
| 2005/0004592 A1 | | 1/2005 | Criscuolo |
| 2005/0051163 A1 | * | 3/2005 | Deem et al. ............ 128/200.24 |
| 2005/0165432 A1 | | 7/2005 | Heinrich |
| 2005/0228445 A1 | | 10/2005 | Mollenauer |
| 2005/0277945 A1 | | 12/2005 | Saadat et al. |
| 2005/0277946 A1 | | 12/2005 | Greenhalgh |
| 2007/0088258 A1 | | 4/2007 | Wenchell et al. |
| 2008/0086167 A1 | | 4/2008 | Mastri et al. |
| 2009/0182279 A1 | | 7/2009 | Wenchell et al. |
| 2009/0270989 A1 | * | 10/2009 | Conner et al. ............ 623/17.16 |

FOREIGN PATENT DOCUMENTS

| | | | |
|---|---|---|---|
| EP | 0 480 653 A1 | | 4/1992 |
| EP | 0 487 175 A1 | | 5/1992 |
| EP | 1 774 918 A1 | | 4/2007 |
| FR | 2 810 555 A | | 12/2001 |
| GB | 2 275 420 A | | 8/1994 |
| WO | WO 02/34108 A2 | | 5/2002 |
| WO | WO 2004/028613 A2 | | 4/2004 |
| WO | WO 2005/013832 A1 | | 2/2005 |
| WO | WO-2008042005 A1 | | 4/2008 |

OTHER PUBLICATIONS

International Search Report dated Sep. 3, 2007.
Written Opinion of the International Searching Authority.
International Search Report for PCT/US2008/60163.
International Search Report for PCT/US2007/02603.
International Search Report for PCT/US2009/060296.

* cited by examiner

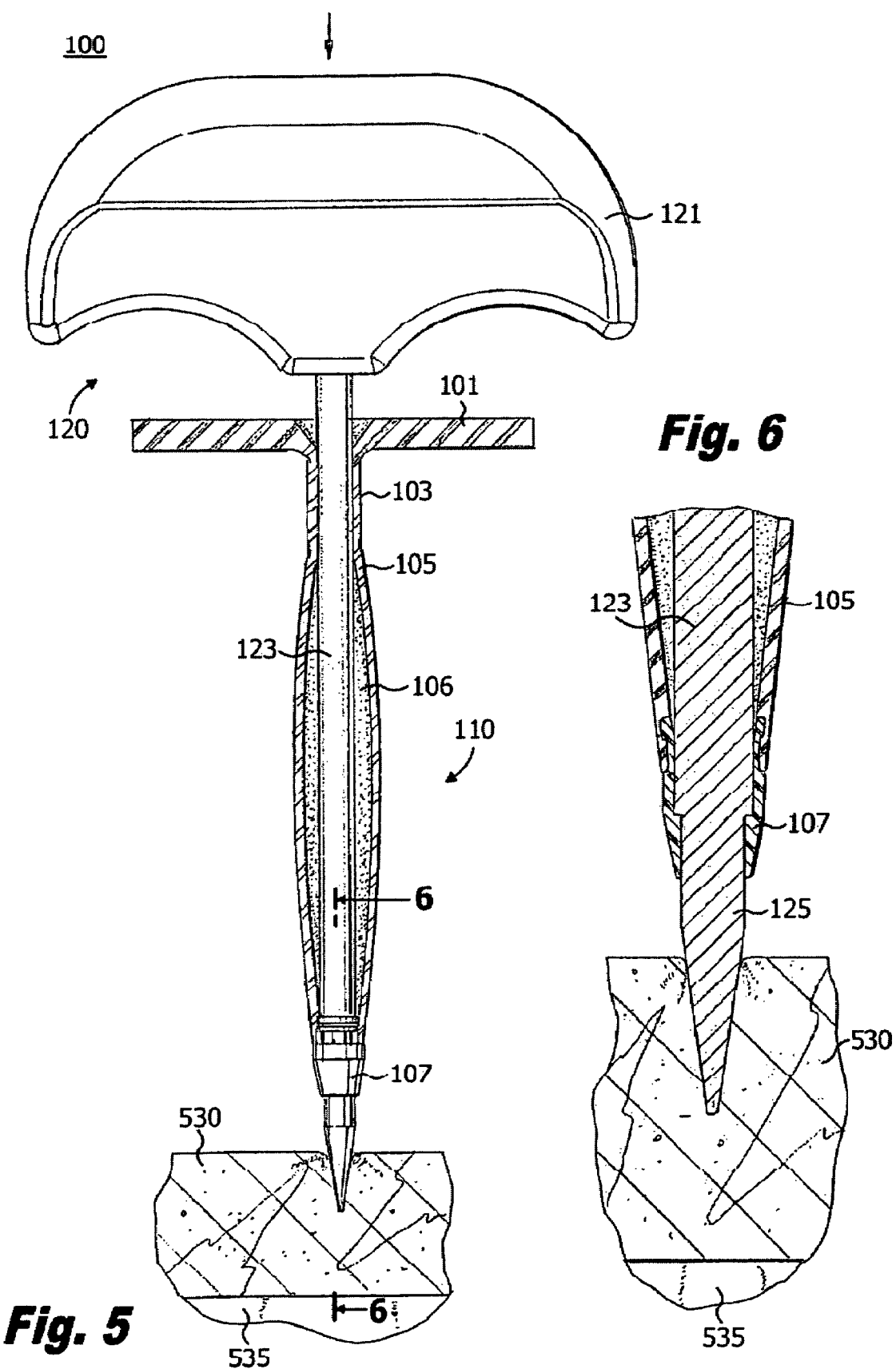

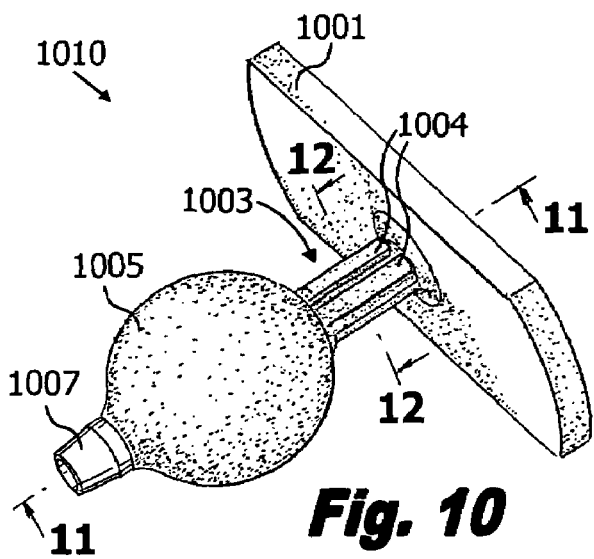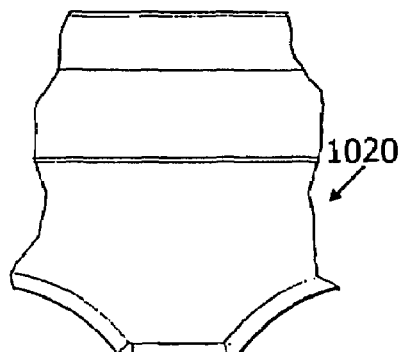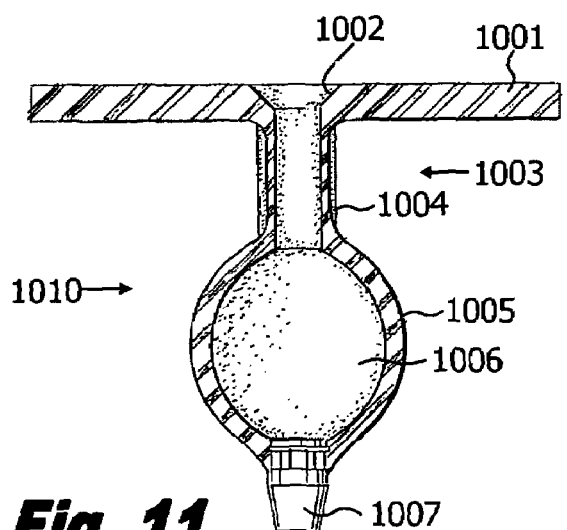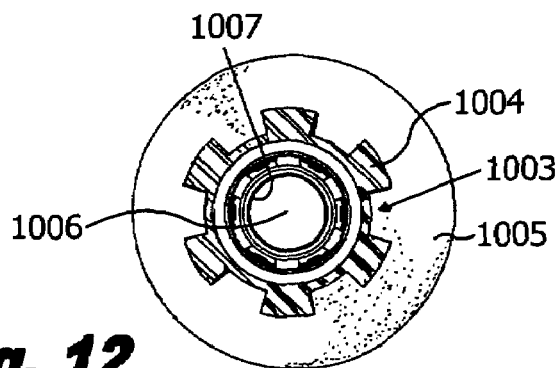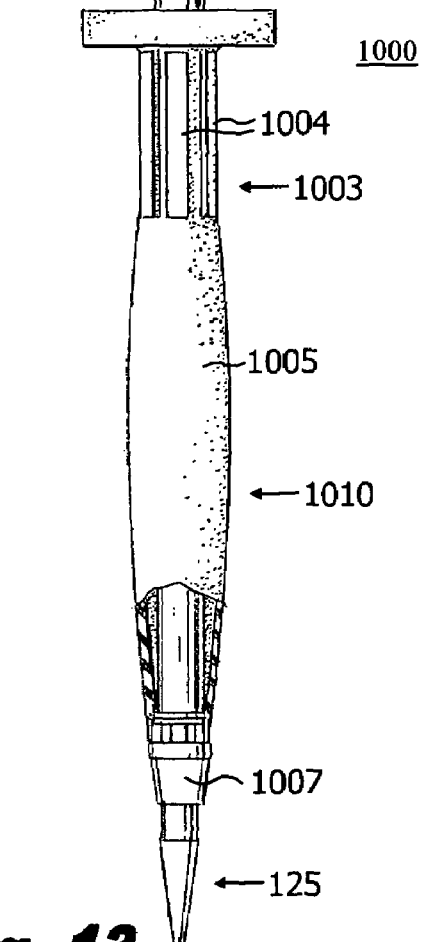
Fig. 10
Fig. 11
Fig. 12
Fig. 13

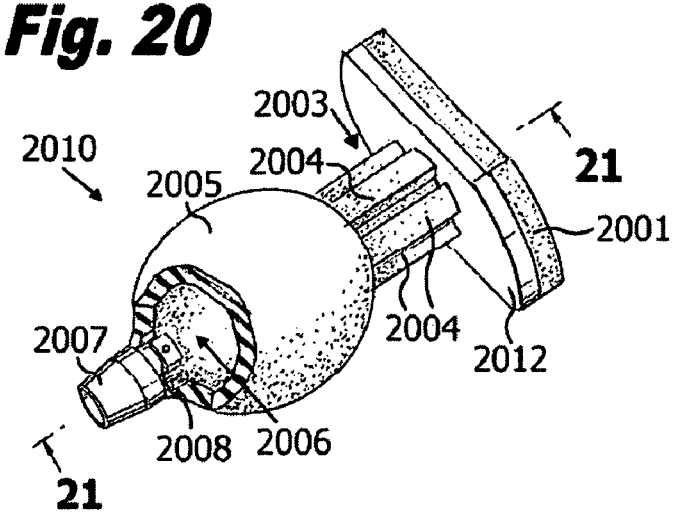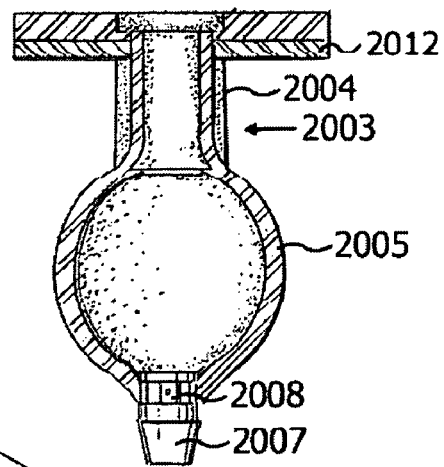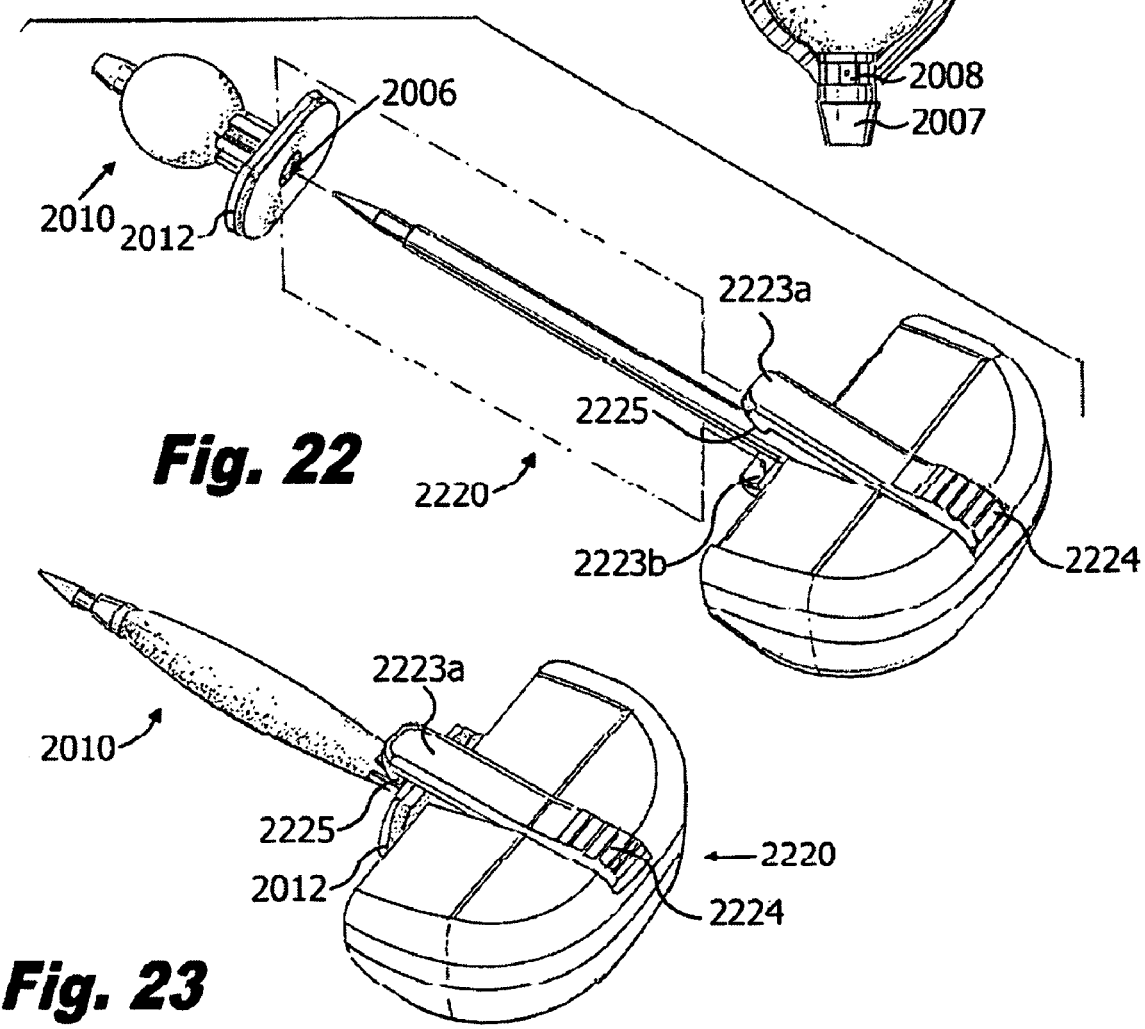

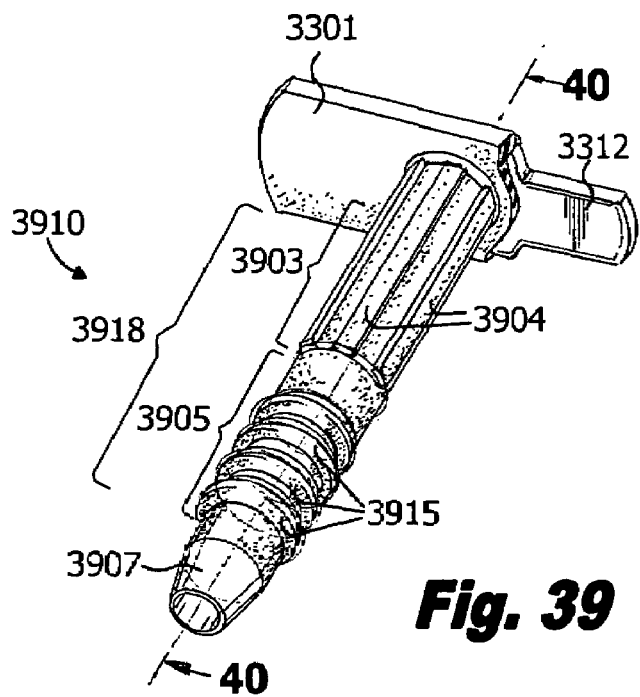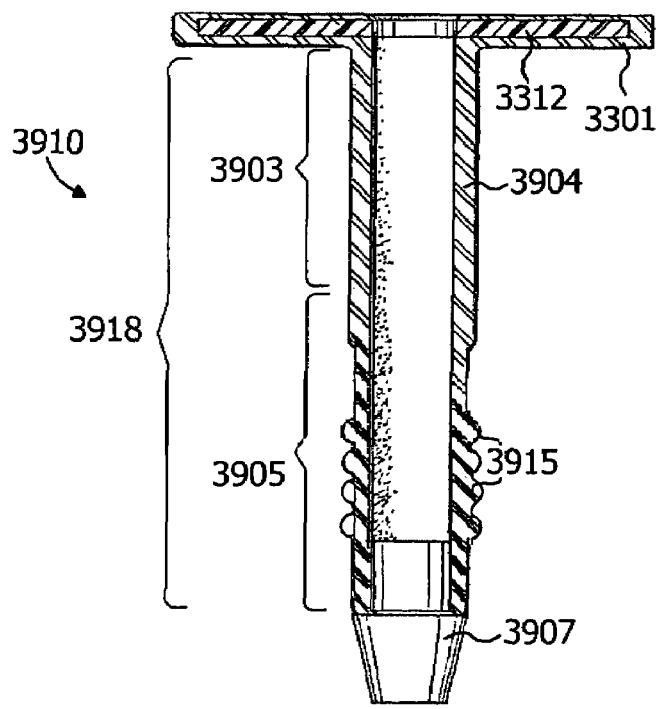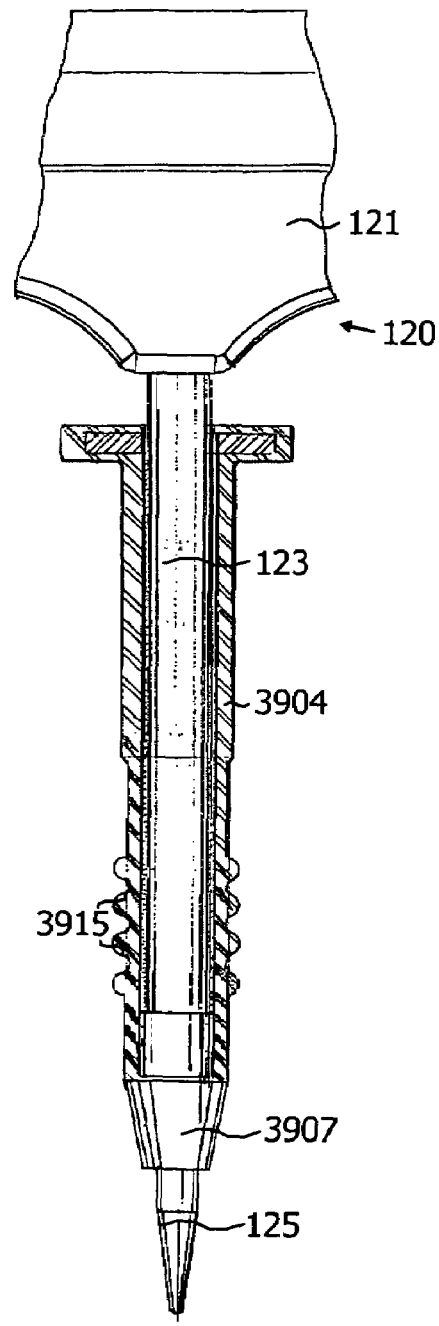
Fig. 39
Fig. 40
Fig. 41

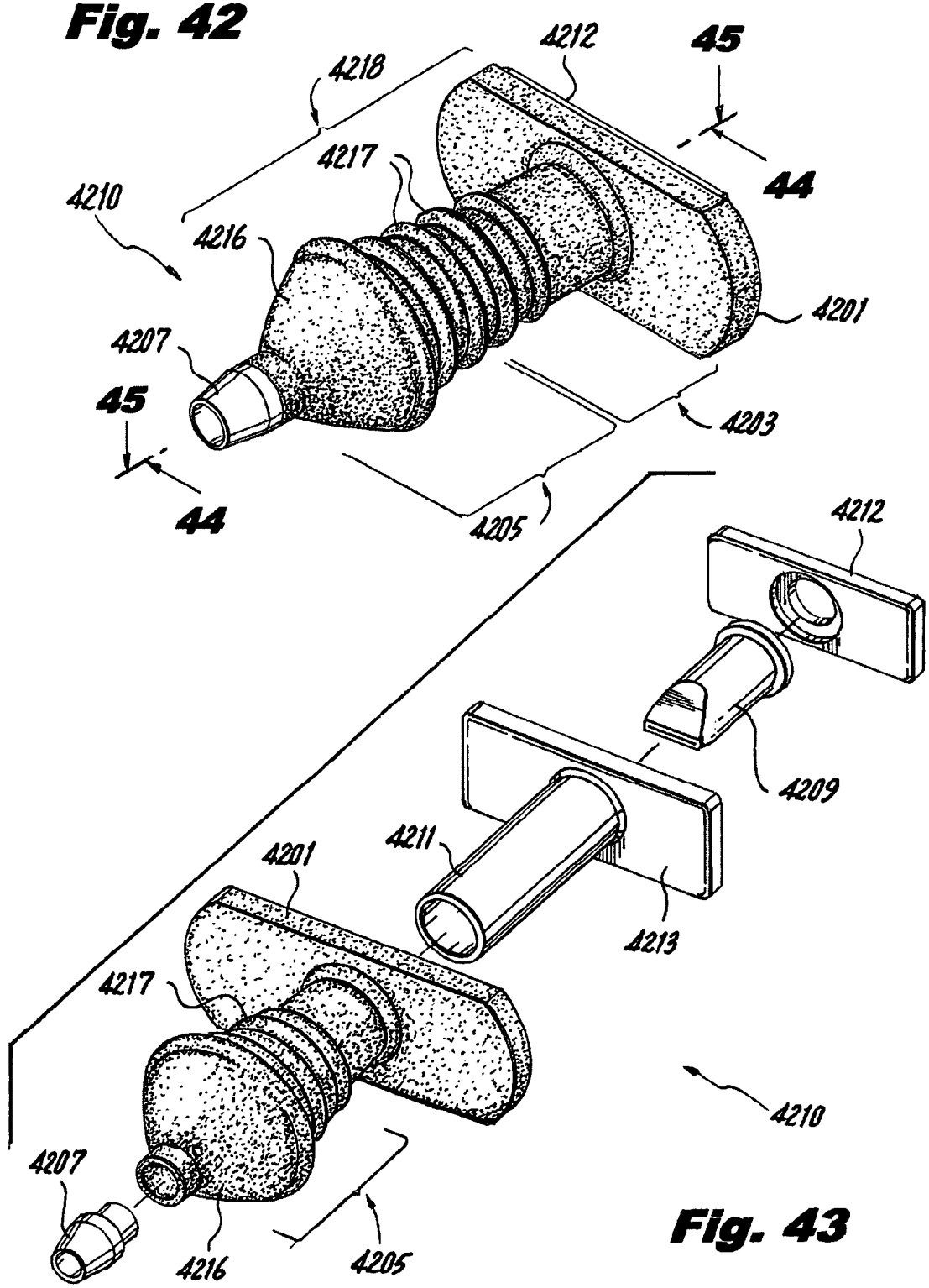

ELASTICALLY DEFORMABLE SURGICAL ACCESS DEVICE

BACKGROUND OF THE INVENTION

1. Field of the Invention

The present invention relates to sealable surgical access devices. Particularly, the present invention is directed to such devices that are capable of deforming to a low-profile configuration to facilitate insertion, for example, into the abdominal wall of a patient.

2. Description of Related Art

A variety of surgical access devices are known in the art for providing access to a surgical cavity during minimally invasive surgical procedures. Such devices typically include a rigid tubular element, which defines a channel or lumen therethrough. The tubular element provides an open channel through the abdominal wall and into a surgical cavity, through which surgical instruments can pass. Typically, a seal is provided to inhibit insufflation gas from exiting to the surrounding environment while surgical instruments are removed from the lumen.

Such conventional devices generally have been considered satisfactory for their intended purpose. However, such devices are relatively costly to manufacture, being made from relatively expensive materials, such as polycarbonate plastic. Such devices also inhibit movement of surgical instruments, due to the long, rigid and narrow lumen defined therein. As a result, a surgeon must tilt the entire rigid access device, in order to manipulate his instruments. Further, such devices are not typically provided with a facility for anchoring to the abdominal wall, and therefore can be accidentally removed therefrom during a procedure. Although some solutions to the foregoing problems have been developed, devices remedying some of these problems have been relatively complex and expensive. Therefore, there remains a continued need in the art for a surgical access device that provides access to a surgical cavity, which is a reduced encumbrance on a surgical procedure. There also remains a need in the art for such a surgical access device that is inexpensive and easy to manufacture. The present invention provides a solution for these problems.

SUMMARY OF THE INVENTION

The purpose and advantages of the present invention will be set forth in and apparent from the description that follows. Additional advantages of the invention will be realized and attained by the devices and methods particularly pointed out in the written description and claims hereof, as well as from the appended drawings.

In accordance with one aspect of the invention, a surgical access device having an access port is provided. The access port has an elongated body with opposed proximal and distal end portions, and defines a longitudinal axis. The body has a central lumen extending therethrough, which in-turn includes a resilient bulb portion formed between the proximal and distal end portions of the body. The resilient bulb portion is adapted and configured to transition between a first condition in which the bulb portion has a first diameter and a first length and a second condition in which the bulb portion has a second diameter and a second length; the second diameter is less than the first diameter, and the second length is greater than the first length. In accordance with this aspect, a first engagement means is arranged in the distal end portion of the body, for engagement with a distal end portion of an insertion device, such as a trocar. The insertion device is adapted and configured to releasably engage the distal end portion of the access port body so as to facilitate a transition from the first condition to the second condition of the bulb portion of the access port body.

In accordance with another aspect of the invention, a surgical access device having an access port and an elongated trocar is provided. The access port has an elongated body with opposed proximal and distal end portions, and defines a longitudinal axis. The body has a central lumen extending therethrough, which in-turn includes a resilient bulb portion formed between the proximal and distal end portions of the body. The resilient bulb portion is adapted and configured to transition between a first condition in which the bulb portion has a first diameter and a first length and a second condition in which the bulb portion has a second diameter and a second length; the second diameter is less than the first diameter, and the second length is greater than the first length. The elongated trocar is adapted to extend into the central lumen of the access port body and configured to releasably engage the distal end portion of the access port body so as to facilitate a transition from the first condition of the bulb portion of the access port body to the second condition of the bulb portion of the access port body.

In accordance with either of the foregoing embodiments the following features can be incorporated therewith, as desired. The bulb portion can have, for example, a generally spherical, generally ovoid, or other shape configuration in the first condition. The bulb portion of the access port body can be formed at least in part from an elastomeric material, such as silicone rubber. The bulb portion can have an outer surface with a substantially convex arcuate contour. The proximal end portion of the access port body can have a substantially constant outer diameter. Further, the bulb portion in the first condition can include an expanded diameter, or can be substantially straight. Additionally or alternatively, the bulb portion can include one or more circumferential longitudinally spaced ribs or longitudinal circumferentially-spaced ribs.

An insert sleeve can be disposed within the distal end portion of the access port body for engaging a distal end portion of the trocar and can be arranged at the distal end of the access port body, forming a tip thereof. Such insert sleeve can be formed from a material having a greater rigidity than the access port body, and can be, for example, Nylon. The insert sleeve can include a plurality of proximally extending expandable guide fingers for lining an inner surface of the bulb portion to accommodate or facilitate insertion of the trocar. Additionally, if desired, an elongated guide tube can be provided, which extends through the proximal portion of the access port body and at least partially into the bulb portion of the access port body.

Further, if desired, a substantially rigid generally planar flange portion can be associated with the proximal end portion of the access port body, and can define an access port communicating with the lumen of the access port body. Such access port can have a conically tapering lead-in surface. If provided, the insertion device can include a handle with releasable locking means for releasably engaging aforementioned flange portion.

If desired or required, the proximal portion of the access port body can be provided with longitudinal, circumferentially spaced ribs formed on an outer surface of the body, for inhibiting elongation of the proximal end portion of the access port body during the transition from the first condition of the bulb portion to the second condition of the bulb portion. Alternatively or additionally, the proximal portion of the access port body can be provided with circumferential, longitudinally spaced ribs formed on an outer surface of the body, for inhibiting circumferential expansion of the proximal end portion of the access port body during the transition from the first condition of the bulb portion to the second condition of the bulb portion. Additionally or alternatively, the body can be provided with circumferential, longitudinally spaced ribs formed on an outer surface of the body, for inhibiting removal of the bulb portion from an abdominal wall of a patient.

In accordance with the invention, a seal member can be disposed within the lumen, in the proximal end portion of the access port body. Such seal member can be, for example, a duckbill type valve, ball valve, or a fluid seal as set forth, for example in U.S. patent application Ser. No. 11/517,929 filed Sep. 8, 2006. Additionally or alternatively, an integrally formed seal can be provided within the lumen, in the proximal end portion of the access port body. Such seal can be, for example, a protrusion provided on the wall of the lumen, to seal a space between the wall of the lumen and a surgical instrument. Alternatively or additionally, sealing can be accomplished by way of a collapsible region defined in the proximal end portion of the body such that the collapsible region can be collapsed by an outside force, to seal the lumen. Such outside force can be, for example, force exerted by the abdominal wall of a patient.

The body can be provided with a first engagement means in the distal end portion thereof, such that a distal end portion of a trocar can engage the first engagement means. Such engagement means can be tabs, which are configured and arranged to be grasped by the trocar, or alternatively, a substantially rigid stepped element, for engaging a mating portion of the trocar. If desired, the body can be provided with second engagement means in the proximal end portion thereof, with a proximal end of the trocar, obturator or other insertion device being adapted for engaging the second engagement means.

In the foregoing embodiments, the trocar or insertion device preferably has a length greater than the first length of the bulb portion of the body, and therefore causes extension of the bulb portion to the second length. If a second engagement means is arranged in the proximal end portion of the body, for engagement with a proximal end portion of the trocar or insertion device, the insertion device can maintain the access port body in the second condition while engaged therewith.

In accordance with still another aspect of the invention, a method of forming an access port in a patient is provided. The method includes:

(a) providing an access port in accordance with the invention, as set forth herein;

(b) providing an insertion device configured to engage the distal end portion of the access port body;

(c) extending the insertion device into the central lumen of the access port body so as to engage the distal end portion of the access port body;

(d) elongating the access port with the insertion device, the end of the insertion device being engaged with the distal end portion of the access port body;

(e) inserting the access port and insertion device through an abdominal wall of a patient to a predetermined position, while maintaining the access port in an elongated configuration; and (f) removing the insertion device from the access port, allowing the access port to revert to the first configuration, with the bulb portion of the access port engaging an interior surface of the abdominal wall.

The method can further include the step of performing surgery by inserting a surgical instrument through the lumen of the access port, and through an optional rigid member associated with a portion of the body. The method can further include sealing the central lumen, either upon itself, or between the access port and a surgical instrument. Such sealing can occur by a radially inwardly directed force acting on the access port, exerted by the abdominal wall of the patient.

Additionally or alternatively, the step of elongating the access port with the insertion device can further include engaging the insertion device with a first engagement means at the distal end of the access port and elongating the port along the insertion device.

Additionally or alternatively, the method can further include the step of engaging a second engaging means associated with the proximal end of the access port with a corresponding engagement means on the insertion device to selectively maintain the access port body in an elongated configuration.

In accordance with the invention, the step of inserting the port can include inserting the access port through the abdominal wall with the insertion device in engagement with the first and second engagement means of the access port.

The methods set forth herein can further include removing the access port from the abdominal wall. Such removal can include reengaging the insertion device with the first and second engagement means to elongate the access port body, and withdrawing the elongated access port from the abdominal wall.

It is to be understood that both the foregoing general description and the following detailed description are exemplary and are intended to provide further explanation of the invention claimed.

BRIEF DESCRIPTION OF THE DRAWINGS

The accompanying drawings, which are incorporated in and constitute part of this specification, are included to illustrate and provide a further understanding of the devices and methods of the invention. Together with the description, the drawings serve to explain the principles of the invention, wherein:

FIG. 5 is a partial cross-sectional view of the surgical access device of FIG. 1, showing the insertion effecting extension of the through the access port, the figure also illustrating an initial insertion being made through an abdominal wall by the insertion device;

FIG. 6 is a detail cross-sectional view of the initial insertion of the surgical access device, the figure also illustrating the engagement between the insertion device and access port at the distal end of the surgical access device;

FIG. 10 is an isometric view of another embodiment of an access port of a surgical access device in accordance with the invention, having longitudinal ribs on a neck portion thereof;

FIG. 11 is a partial cross-sectional view of the access port of FIG. 10, taken along line 11-11 of FIG. 10;

FIG. 12 is a cross-sectional view of the access port of the access port of FIG. 10, taken along line 12-12 of FIG. 10;

FIG. 13 is a cutaway view of the access port of FIG. 10, shown in an elongated configuration, with an insertion device inserted therein;

FIG. 20 is a cutaway view of still another embodiment of an access port in accordance with the invention, including a reinforcing back stop for engagement with an insertion device in accordance with the invention;

FIG. 21 is a partial cross-sectional view of the access port of FIG. 20, taken along line 21-21;

FIG. 22 is an isometric view of a surgical access device in accordance with the invention, including the access port of FIG. 20, and an insertion device having a latching mechanism for engaging the access port;

FIG. 23 is an isometric view illustrating the surgical access device of FIG. 22, showing the access port in an elongated configuration in engagement with an insertion device, prepared for insertion through the abdominal wall of a patient;

FIG. 39 is an isometric view of still another access port in accordance with the invention, having longitudinal ribs in a neck portion and circumferential ribs in the distal end portion thereof;

FIG. 40 is a partial cross-sectional view of the access port of FIG. 39 taken along line 40-40 thereof;

FIG. 41 is a partial cross-sectional view of the access port of FIG. 39, shown in an elongated configuration with an insertion device inserted in the access port;

FIG. 42 an isometric view of a further embodiment of access port in accordance with the invention, which access port has an enlarged, generally barb-shaped region and a plurality of barb-shaped ribs to inhibit pullout of the access port from the abdominal wall of a patient;

FIG. 43 is an exploded view of the access port of FIG. 42, illustrating the various components thereof;

DETAILED DESCRIPTION OF PREFERRED EMBODIMENTS OF THE INVENTION

Reference will now be made in detail to the selected embodiments of the invention, examples of which are illustrated in the accompanying drawings.

The devices and methods presented herein relate to providing a surgical access port to allow insertion and removal of surgical instruments during a procedure. The present invention is particularly suited for use in minimally-invasive surgical procedures of the abdomen, and is suitable for procedures where the abdominal cavity is pressurized with insufflation gas.

Figure 1:
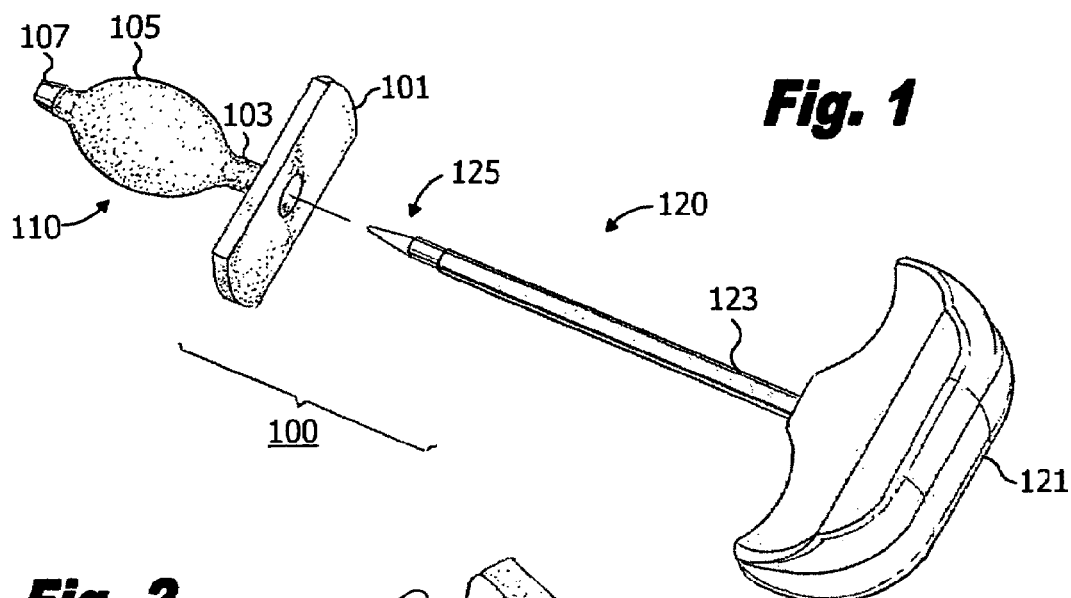
FIG. 1 is an isometric view of a first representative embodiment of a surgical access device in accordance with the present invention, including an insertion device and an access port.
Figure 2:
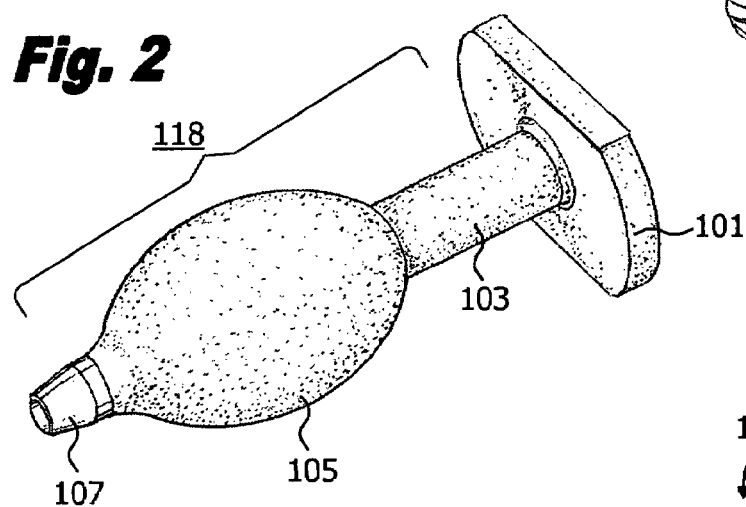
FIG. 2 is an isometric view of the access port of FIG. 1.

For purpose of explanation and illustration, and not limitation, an isometric view of an exemplary embodiment of a surgical access device in accordance with the invention is shown in FIG. 1 and is designated generally by reference character 100. Other embodiments of surgical access devices in accordance with the invention, or aspects thereof, are provided in FIGS. 2-34, as will be described.

FIGS. 1-9 illustrate the surgical access device 100, and components thereof alone, and in conjunction with an abdominal wall (i.e., 530 of FIGS. 5-9) of a patient, additionally illustrating the steps of insertion and use the surgical access device 100. The surgical access device 100 includes, generally, an access port 110 and an inserter 120. The access port is at least partially flexible in its construction, and depending on the particular embodiment can be primarily composed of one or more flexible materials. The access port includes a body 118, with a proximal flange 101 and distal tip 107 arranged thereon, at opposed ends thereof. The body 118 includes bulb portion 105 and a neck portion 103, each of which defines a respective portion of a lumen 106 passing therethrough. Upon insertion, as will be understood, the bulb portion 105 assists in anchoring the access port 110 into the abdominal wall 530 (e.g., in FIG. 8) of the patient, while the neck portion 103 maintains a passageway through the abdominal wall 530.

The insertion device 120 includes a handle 121 for gripping by a user, a shaft 123, and a distal tip 125. The tip 125 can include an engagement feature, such as the stepped portion illustrated, which engages a mating stepped interior of the distal tip 107 of the access port 110. The insertion device can include a cutting tip at its distal end, or can have a blunt tip at the end thereof. The insertion device 120, therefore, can be a trocar, a blunt-tip obturator, or a visualization device (e.g., an obturator with a visualization tip and a channel to receive an endoscope), for example. The flange 101, serves multiple purposes. Firstly, the flange 101 serves as a location for a user to grip when preparing the access port 110 for insertion. Secondly, the flange 101 acts as a stop to abut the outer surface (skin) of the patient's abdominal wall, preventing the entire access port 110 from passing through the incision made to insert the access port. Further, the flange 101 can be provided with a lead in surface 102, which helps guide the insertion device 120, or other instruments therein and therethrough.

The tip 107 is provided at the distal end of the body 118 of the access port 110. The tip 107 is insert molded, adhered, or otherwise secured to the body 118, details of which are set forth below in connection with other embodiments. Since the tip 107 must securely engage the insertion device 120, the tip 107 is preferably made of a relatively rigid material. However, although illustrated as extending distally from the body 118, the tip can be provided within the body 118, near the distal end thereof, if desired. As such, the tip 107 can be concealed from view, while still having the necessary rigidity to withstand forces exerted by the insertion device 120, for example. Variations of the bulb portion 105, neck portion 103, tip 107 and flange 101 are described below in connection with other embodiments. Naturally, these specific features can be interchanged and combined as needed or desired.

Figure 3:
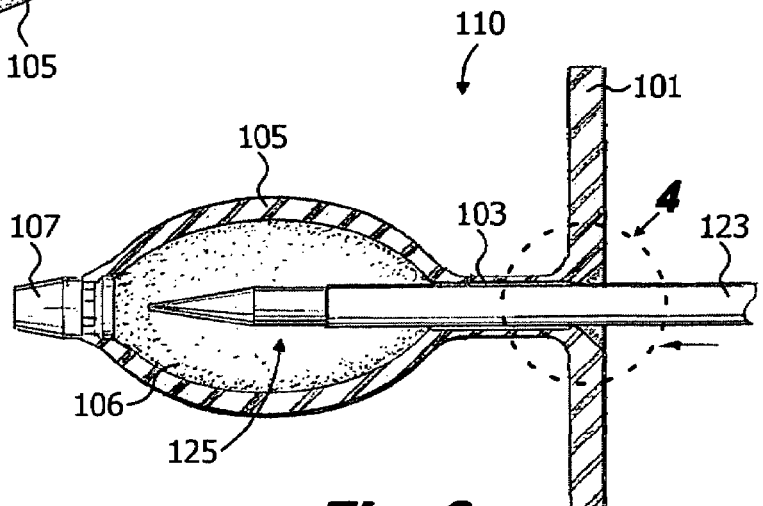
FIG. 3 is a partial cross-sectional view of the surgical access device of FIG. 1, showing the insertion device advancing through the access port.
Figure 4:
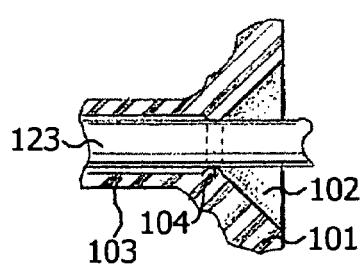
FIG. 4 is a detail view of region 4 in FIG. 3.

FIG. 4 is a detail view of the respective region of FIG. 3. As can be seen, the lead in surface 102 can facilitate insertion of a surgical instrument. Additionally, an integral O-ring seal 104 is provided, which seals between an instrument shaft (illustrated as insertion device shaft 123), and the access port 110. Thus, egress of insufflation gas is inhibited. Naturally, such feature can be applied to any embodiment set forth herein. Additionally, the precise configuration of the seal 104 can vary, if desired, but the seal 104 can, as illustrated, be a simple projection of the seal 104 from the neck portion 103 of the access port 110. Moreover, a plurality of seals, such as seal 104 can be provided in series to further enhance sealing capability.

As shown in FIGS. 5 and 6, in use, the insertion device 120 is inserted through the lumen 106 of the access port 110, with the tip 125 of the insertion device 120, passing through and engaging the tip 107, preventing proximal movement of the tip 107, relative to the insertion device 120 (FIG. 6). Next, the flange 101 is pulled proximally by the user, toward the handle 121 of the insertion device 120, longitudinally elongating the access port 110, reducing its cross-sectional profile, to facilitate insertion (e.g., in FIG. 5). The access port 110 is maintained in an elongated configuration during insertion, as the surgical access device passes through the abdominal wall 530 of the patient. Because the access port 110 includes a flexible material, the access port 110 can be additionally radially compressed by the abdominal wall during insertion.

Figure 7:
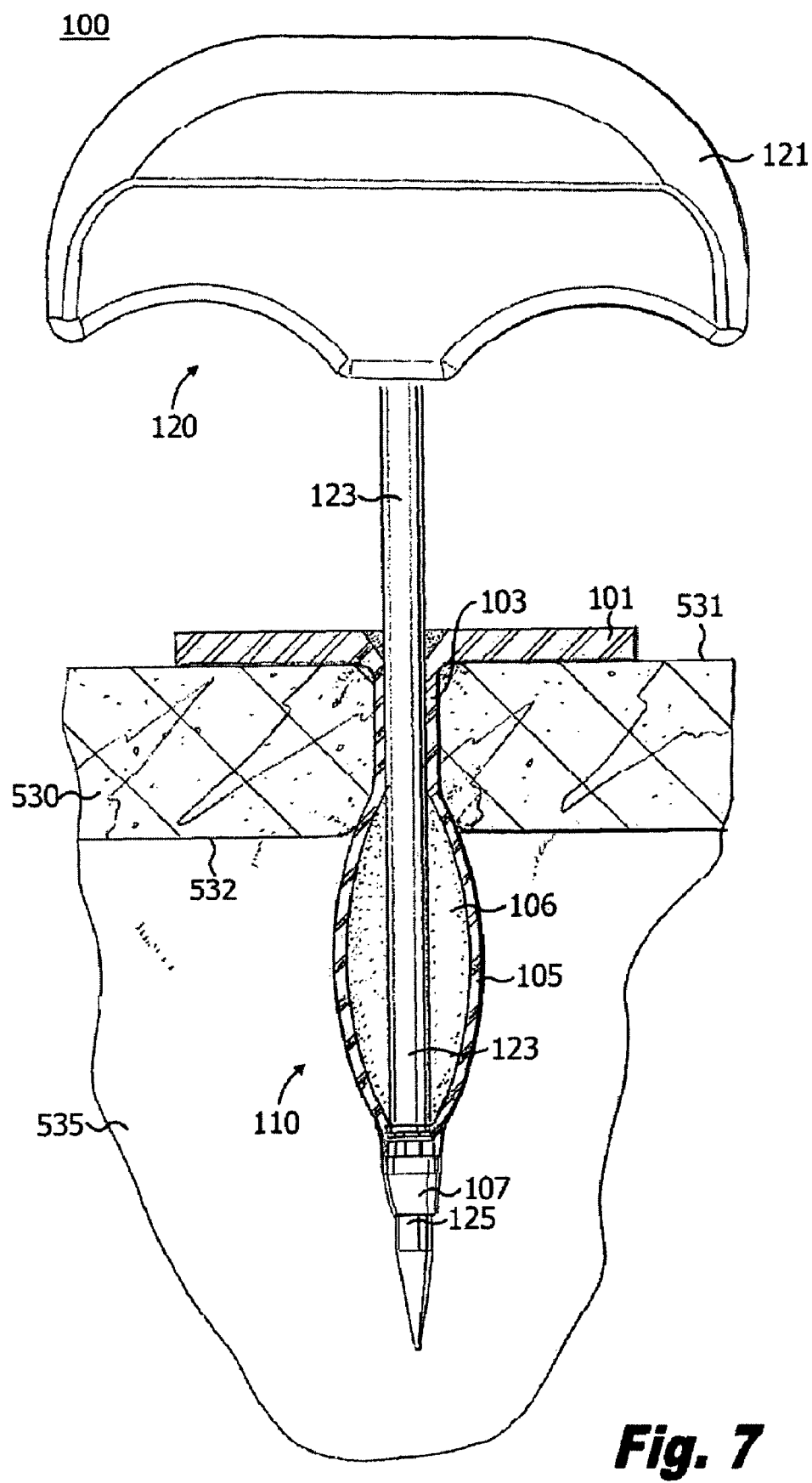
FIG. 7 is a partial cross sectional view illustrating the surgical access device of FIG. 1, inserted through the abdominal wall, with the insertion device partially withdrawn from the access port.

The surgical access device 100 is urged through the abdominal wall 530 of the patient until the flange 100 meets the surface 531, or skin of the abdominal wall 530. FIG. 7 illustrates the surgical access device 100 in such a position, with the insertion device 120 slightly withdrawn from the access port 110. As the insertion device is withdrawn, the bulb portion 105, now held within the abdominal cavity 535, reverts toward its original configuration, expanding in diameter. The bulb portion 105, therefore, engages the inside surface 532 of the abdominal wall 530. If the access port 110 is configured in such a way that the neck 103 elongates during insertion, upon release of tension in the access port applied by the insertion device 120, the neck 103 attempts to contract, thereby pulling the bulb portion 105 toward the flange 101, helping secure the access port 110 to the abdominal wall 530. If provided, however, ribs (e.g., ribs 1004 shown in FIG. 10) can inhibit the elongation of the neck 103, allowing the force exerted in longitudinally elongating the access port 110 to be focused on reducing the cross sectional profile of the bulb portion 105. Advantageously, as the bulb reverts to its original configuration with the bulb expanded in diameter, the surgical access port foreshortens, the benefits of which will be described below.

Figure 8:
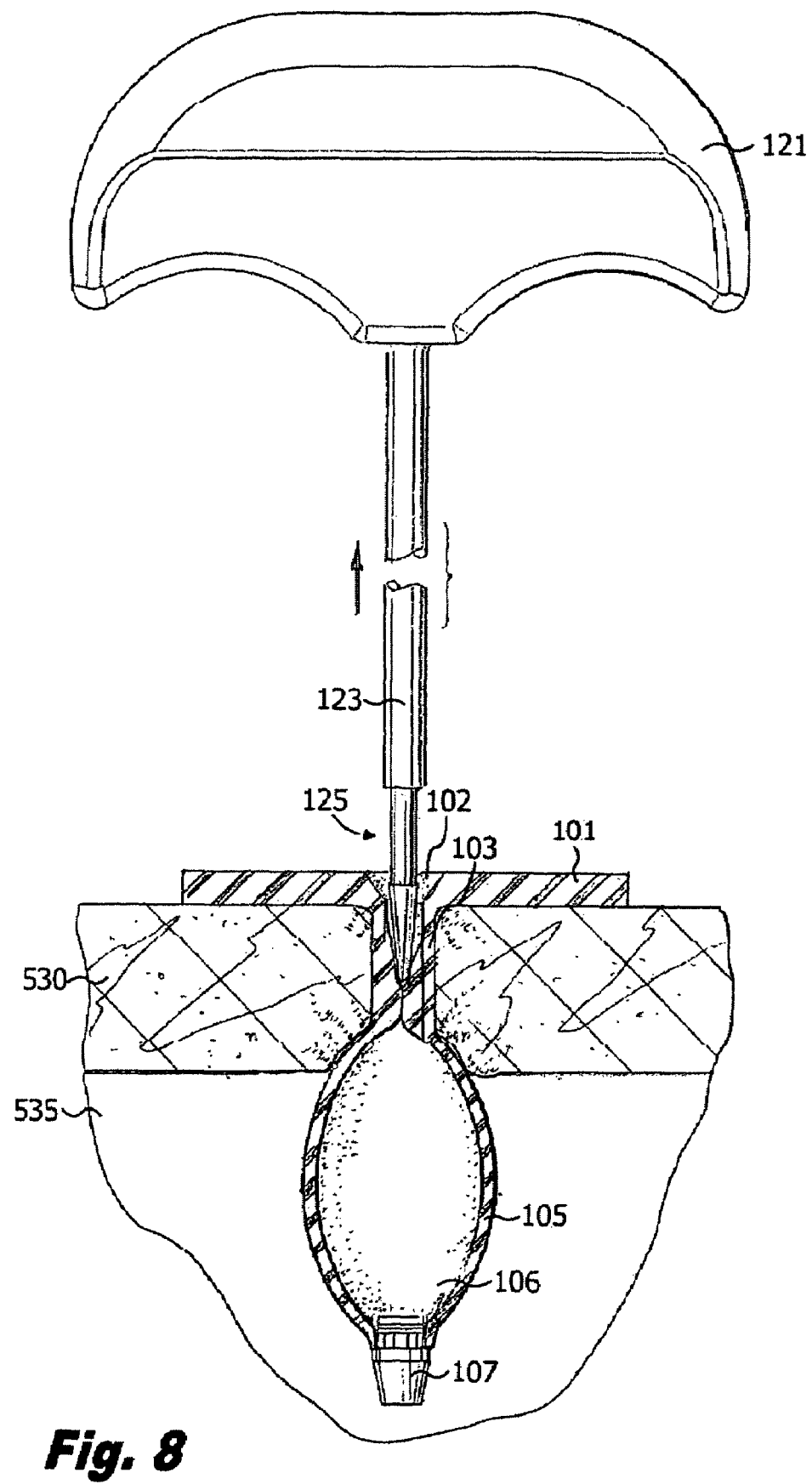
FIG. 8 is a partial cross sectional view illustrating the surgical access device of FIG. 1, inserted through the abdominal wall, with the insertion almost fully withdrawn from the access port.
Figure 9:
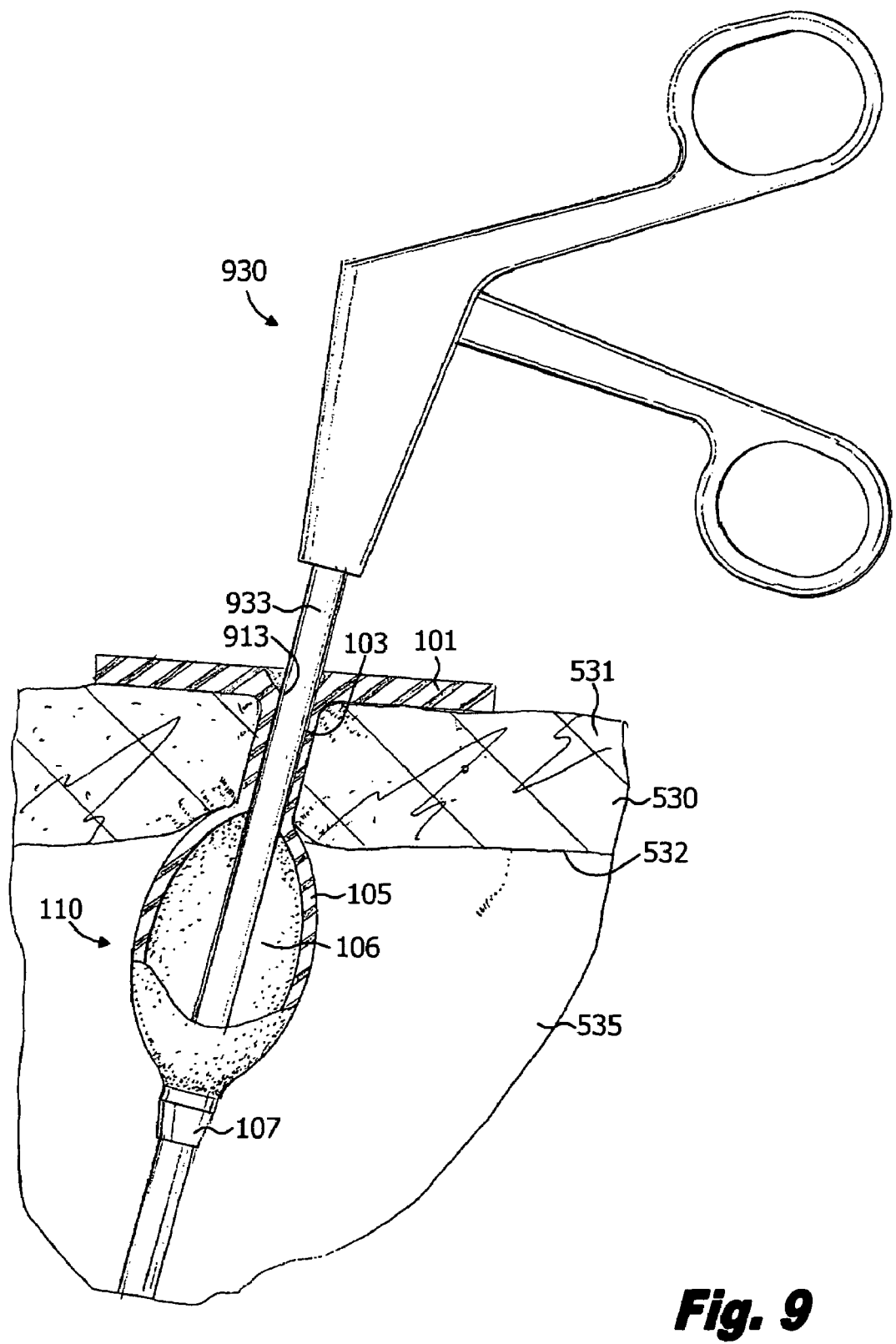
FIG. 9 is a cutaway view the access port of the surgical access device of the preceding figures, illustrating the access port in use, with a surgical instrument inserted therethrough.

FIG. 9 illustrates the access port 100 of FIGS. 1-8, with a surgical instrument 930 inserted therethrough. As illustrated, the flange 101 maintains engagement with the upper and lower surfaces 531, 532 of the abdominal wall 530, even when the access port 110 is manipulated to angle an instrument. Because the surgical access port foreshortens during insertion and is firmly held in place relative to the abdominal wall by the bulb portion 105 and flange 101, the length of the access device interacting with the surgical instrument is minimized and the forces, which must be exerted to angle and manipulate the surgical instrument can therefore be reduced. Further, as can be seen, access ports in accordance with the invention can be sized such that contact is maintained between the interior neck wall 913 and the shaft 933 of the instrument 930, thereby maintaining an airtight seal. Additional seal elements, such as one or more internal ribs, can be arranged circumferentially on the inner wall 913 of the neck 103, if desired. If a plurality of ribs are provided, they can be longitudinally spaced from one another so as to provide even greater sealing.

In this embodiment, upon withdrawal of the instrument 930, the abdominal wall 530, which continually exerts an inward force on the access port 110, causes the lumen 106 in the region of the neck 103 to close, thus sealing the lumen 106, inhibiting escape of insufflation gas from the surgical cavity (e.g., a pneumoperitoneum). Such behavior can be seen, for example, in FIG. 8, illustrating withdrawal of the insertion device 120 from the access port 110. This occurs if the neck portion 103 is configured so as to allow this to happen. For example, the material selection must be such that the neck region is sufficiently compliant, compressible and/or collapsible to be affected by the force of the abdominal wall 530—that is, not excessively rigid. For this reason, it may be desirable to not include longitudinal ribs (e.g., ribs 1004 shown in FIG. 10).

In other instances, however, ribs or other stiffening means may be desirable. As an alternative to ribs, if desired, a material having directional reinforcement can be utilized, such as a fiber-reinforced polymer. As such, the access port 110 can be formed so as to have longitudinal resistance to elongation, for example at the neck 103, while still easily collapsing radially, so as to seal between the access port and a surgical instrument.

It should be noted, that if the neck 103 of the access port 110 is configured so as to be relatively compliant, the neck can adapt to different sizes of surgical instruments inserted therethrough—expanding to the appropriate size to accommodate each tool.

FIGS. 10-13 illustrate an alternate embodiment of a surgical access device in accordance with the invention, designated generally by reference number 1000, which access device 1000 includes an insertion device 1020 and access port 1010. The access port 1010 is similar to the access port 110 of FIGS. 1-9 in many respects. However, in this embodiment, the bulb portion 1005 is more spherical than that of access port 110, which itself is somewhat more elongate in shape. Naturally, the precise shape can be tailored as seen appropriate. The more spherical shape of the bulb portion 1005 of the access port 1010 of FIGS. 10-13 is particularly advantageous in areas where reduced clearance is present, such as, for example, along lateral sides of the abdominal cavity. In the medial portion of the abdominal cavity, particularly if the abdominal cavity is insufflated, more space is available than is available in the lateral regions of the abdominal cavity. The shortened shape of the bulb portion 1005, allows placement of the access port 1010, and allows manipulation of the access port 1010 and tools inserted therethrough, within the cavity.

Additionally, elongation-prevention ribs 1004 are provided on the neck 1003. As evident, particularly from the cross-sectional view of FIG. 12, the increased cross-sectional area of the neck 1003 affords increased resistance to the applied tension needed to elongate the access port 1010 prior to insertion, while not substantially affecting the ability of the neck 1003 to contract or expand radially. As mentioned briefly above, all or a portion of the access port 1010 can be composed of one or more materials having directional properties. For example, the neck 1003 can be provided with reinforcing fibers embedded within the material thereof. Such fibers can be as rigid as desired, to impart the desired properties on the access port.

Alternatively or additionally, the bulb 1005 or flange 1001 can similarly include materials having directional properties. If, for example, the bulb 1005 is reinforced or is otherwise composed of material(s) having directional properties, when tension is applied to the access port 1010 the bulb 1005 will simply deform to a point, elongating as a whole, but without the material itself elongating or "stretching." Thus, it can therefore be understood that elongation or "stretching" of the material itself used for this and other access ports described herein, is not essential to practice of the invention.

FIG. 12 is a cross-sectional view taken across the neck 1003 of the access port 101 of FIG. 10. The ribs 1004 of the neck 1003 are evident thereon, and the tip 1007 can be seen though the lumen 1006 of the access port 1010. FIG. 13 illustrates the access port 1010 of FIG. 10 in an elongated configuration. As can be seen, the relatively spherical shape of the bulb portion 1005 does not yield an access port 1010 that is incapable of assuming a low-profile shape.

Figure 14:
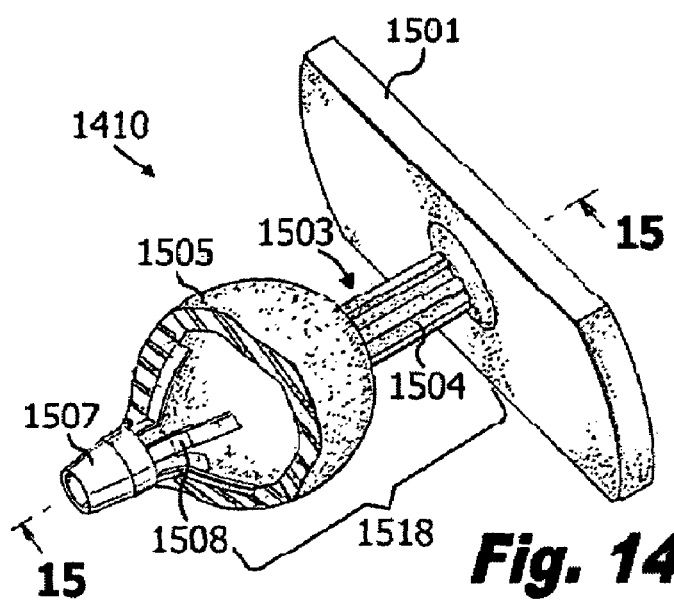
FIG. 14 is a cutaway view of a further embodiment of an access port in accordance with the invention, having inwardly projecting guide fingers for facilitating insertion of surgical instruments through the access port.
Figure 15:
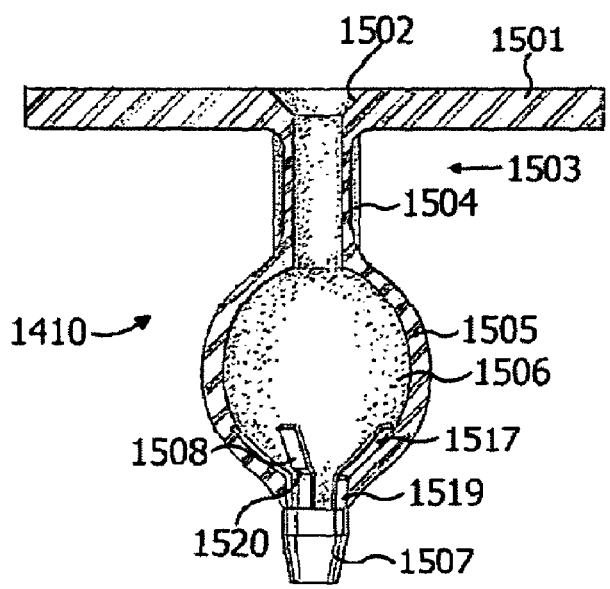
FIG. 15 is a partial cross-sectional view of the access port of FIG. 14 taken along line 15-15 thereof.
Figure 16:
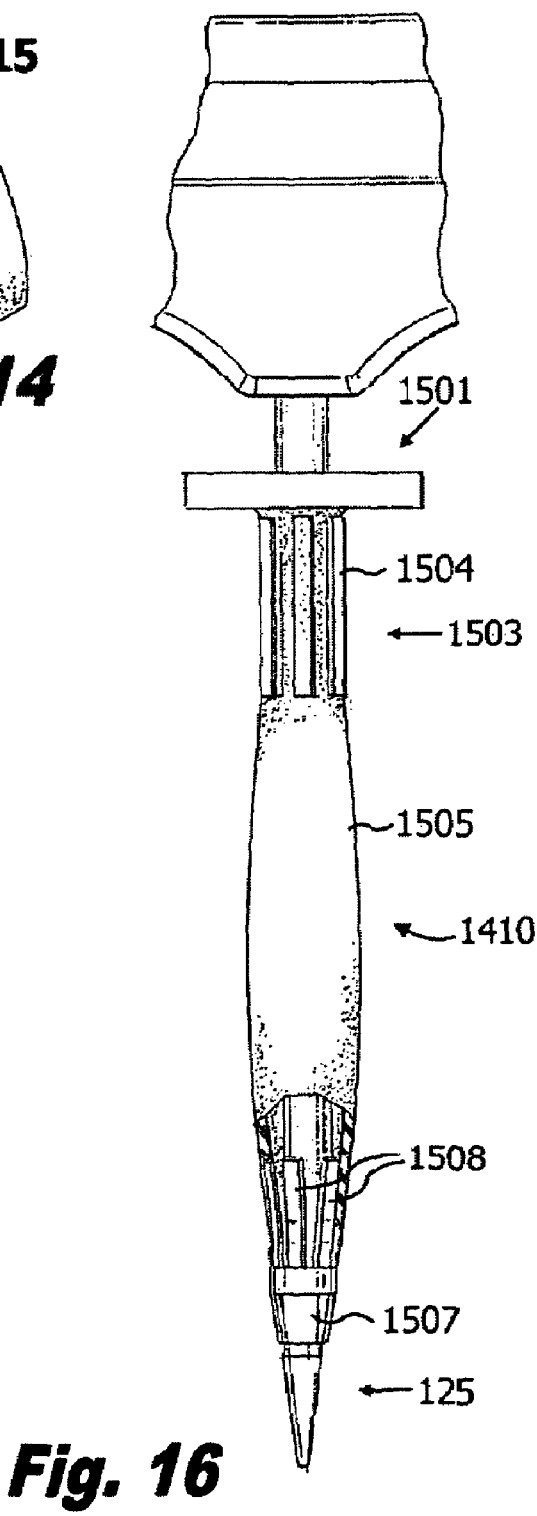
FIG. 16 is a cutaway view of the access port of FIG. 14, shown in an elongated configuration, with an insertion device inserted therein.

FIGS. 14-16 illustrate a further embodiment of an access port 1410 in accordance with the invention. The general shape of the access port 1410 is similar to that of the access port 1010 of FIGS. 10-13. The access port 1410 includes a flange 1501 with a lead-in surface 1502, a body 1518 having a neck portion 1503 with longitudinal ribs 1504, and a bulb portion 1505. A distal tip 1507 is also provided thereon for engaging an insertion device.

However, the access port 1410, and more specifically the tip 1507, includes axially inwardly and radially outwardly directed flexible fingers 1508, which are provided to line the distal end portion of the lumen 1506, defined within the bulb portion 1505. The fingers 1508 serve to guide surgical instruments toward the lumen of the tip 1507, so as to more easily pass through the access port 1410 and into surgical cavity. While the access port body 1518—the bulb 1505 and the neck 1503—may be made of a material that is relatively soft to allow flexure, the fingers 1508 and additionally the tip 1507 itself can be made of a relatively rigid material. Such material preferably also has a relatively low coefficient of friction against materials used in surgical instruments (e.g., metals and plastics), so that the instruments are easily guided through the lumen and into the surgical cavity.

The fingers 1508 also serve to reinforce the distal end portion of the bulb portion 1505, if they are embodied such that they are at least partially secured to the bulb 1505. Alternatively, they can simply be in contact with the inner surface 1506 of the bulb 1505, resiliently contacting the surface 1506. In the illustrated embodiment, particularly as seen in FIG. 15, the fingers 1508 each include a longitudinal, inwardly projecting portion 1519, extending from the tip 1507. The longitudinal portion 1519 is connected to a second, angled portion 1517 at a resilient hinge 1520, the geometry of which is configured to maintain the angled portion 1517 of each finger 1508 in abutment with the interior surface 1506 of the bulb portion 1505, if the fingers 1508 are not already secured thereto. The hinge 1520 can be a so-called living hinge, defined in the material of the finger 1508 by a reduced thickness region, for example. Alternatively, the fingers 1508 and hinges 1520 can simply be made of material that is flexible enough to bend during elongation of the access port 1410.

With reference to FIG. 16, it can be seen that when the access port 1410 is elongated to result in a reduced cross-sectional profile prior to insertion, the fingers 1508 flex in conjunction with the bulb 1505. The relative dimensions of the fingers 1508 can be selected as desired. For example, the fingers can widen toward their distal ends (distal with respect to the tip 1507), in order to better guide instruments through the lumen 1506. When in the elongated state, as shown in FIG. 16, such widened fingers can lay adjacently to one another, or can be configured to overlap one another. As such, the fingers cover an increased area, while the access port 1410 is in a first configuration (FIGS. 14, 15), and still allow the elongated, reduced profile configuration of FIG. 16.

Figure 17:
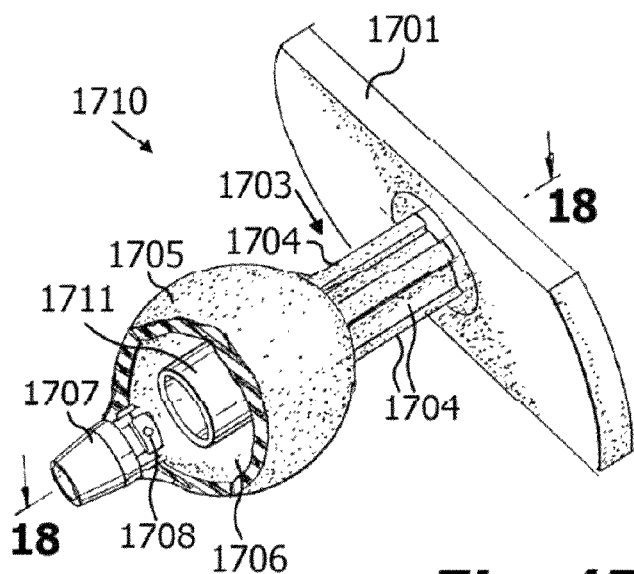
FIG. 17 is a cutaway view of a further embodiment of an access port in accordance with the invention, having a valve and a central guide tube for facilitating insertion of surgical instruments through the access port.
Figure 19:
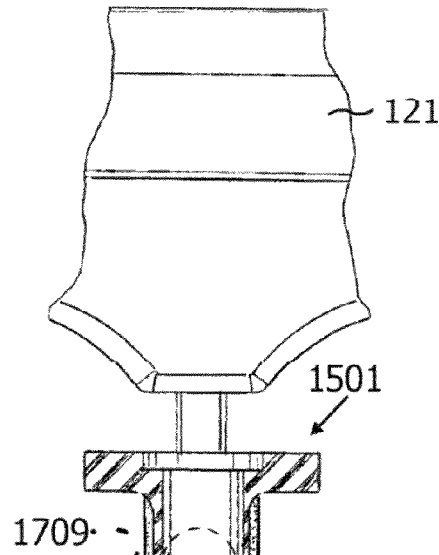
FIG. 19 is a partial cross-sectional view taken along line 18-18 of the access port of FIG. 17, shown in an elongated configuration, having an insertion device inserted therein.
Figure 18:
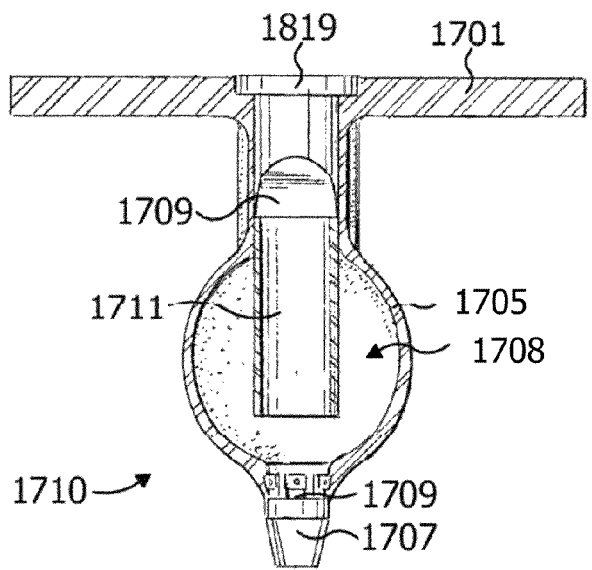
FIG. 18 is a partial cross-sectional view taken along line 18-18 of the access port of FIG. 17.

With reference to FIGS. 17-19, a further embodiment of an access port 1710 in accordance with the invention is provided. The access port 1710 includes a proximal flange 1701, a neck 1703 having longitudinal ribs 1704, and a bulb portion 1705 terminating in a distal tip 1707. The distal tip 1707 is attached to the bulb 1705 in this embodiment by extensions 1708, which provide a location for the material of the bulb 1705 to engage the tip 1707. Such engagement can be effected, for example, by way of insert molding the tip 1707 with the material of the body—that is, the bulb 1705 and neck 1703. In the case of the flange 1701, as with other flanges set forth herein in connection with other embodiments, the flange 1701 can be molded integrally with the neck 1703 and bulb 1705 portions.

The access port 1710 of FIGS. 17-19 differs from the forgoing embodiments in that the access port 1710 includes a guide tube 1711 and a valve 1709 provided in the lumen 1706 thereof. The guide tube is provided with a proximal flange 1819, which rests in a recess formed in the flange 1701 of the access port 1710. The flange 1819 of the guide tube 1711 maintains the tube 1711 in place, and can be insert molded, adhered or otherwise attached to the access port body. The tube 1711 serves as a guide during insertion of surgical instruments, helping lead the instruments toward the tip 1707, reducing the chances that such instruments will veer toward the inner wall 1706 of the bulb 1705, which might delay the surgical procedure being performed. The guide tube 1711 is also preferably made out of material having a relatively low coefficient of friction, with respect to the surgical instruments being inserted therethrough, in order to further facilitate insertion of surgical instruments.

The valve 1709, is shown as a duckbill type valve, but can be of any type desired. Alternatively or additionally, a ball valve and/or or a fluid seal can be utilized, as set forth, for example in U.S. patent application Ser. No. 11/517,929 filed Sep. 8, 2006, which is incorporated herein by reference in its entirety. The valve 1709 is arranged within the guide tube 1711 and serves to reduce leakage of insufflation gas from the surgical cavity (e.g., a pneumoperitoneum), when instruments are removed from the access port 1710. While certain of the foregoing embodiments, such as the access port 110 of FIGS. 1-9, seal upon removal of an instrument due to the compressive forces exerted by the abdominal wall, the guide tube 1711, which is relatively rigid, prevents this embodiment from sealing in that manner. Accordingly, the valve 1709 is provided to seal when an instrument is removed from the access port 1710.

FIGS. 20-23 illustrate a surgical access device, including an access port 2010 and an insertion device 2220. The access port 2010 is similar in many respects to the foregoing access ports, with the exception of a reinforcing backstop 2012 provided on the underside of the flange 2001. The backstop 2012 rigidities the flange 2001, and provides a secure surface for engagement with locking pawls 2223a, 2223b of the insertion device 2220. The pawls 2223a, 2223b are preferably resiliently biased toward a closed position, where protrusions 2225 at the distal end thereof engage the backstop 2012, inhibiting removal of the insertion device 2220 from the access port 2010. A user can disengage the pawls 2223a, 2223b by depressing the release end 2224 of the pawls 2223a, 2223b, which pivot the protrusions 2225 away from the access port 2010 and the backstop 2012.

While the above-described latching mechanism can be incorporated into any of the embodiments set forth herein, the access port 2010 illustrated includes a flange 2001, which holds the backstop 2012, a neck 2003 having longitudinal ribs 2004, a bulb portion 2005, and a tip 2007, secured to the bulb portion 2005 with extensions 2008.

In use, the user places the insertion device 2220 through the lumen 2006 of the access port 2010, elongating the access port 2010 until the pawls 2223a, 2223b engage the backstop 2012 (See FIG. 23). The access device is then inserted through the abdominal wall of the patient. The user then depresses the release ends 2224 of the pawls 2223a, 2223b, and withdraws the insertion device 2220 from the access port 2010, allowing the access port 2010 to revert toward its original configuration (as in FIG. 20, for example). The access port may deviate slightly from its original configuration when inserted because of the forces acting on the access port 2010. However, it is to be understood that the configuration of the access port 2010 prior to elongation is very similar to that of the access port 2010 when inserted through the abdominal wall.

Figure 24:
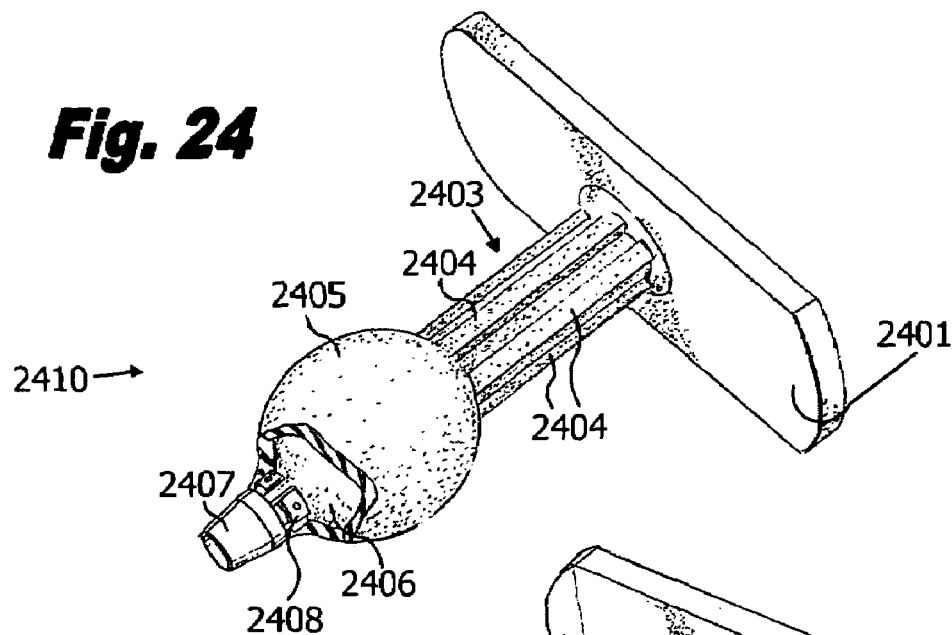
FIG. 24 is an isometric view of a further embodiment of an access port in accordance with the invention, having a relatively longer neck portion than foregoing embodiments.
Figure 25:
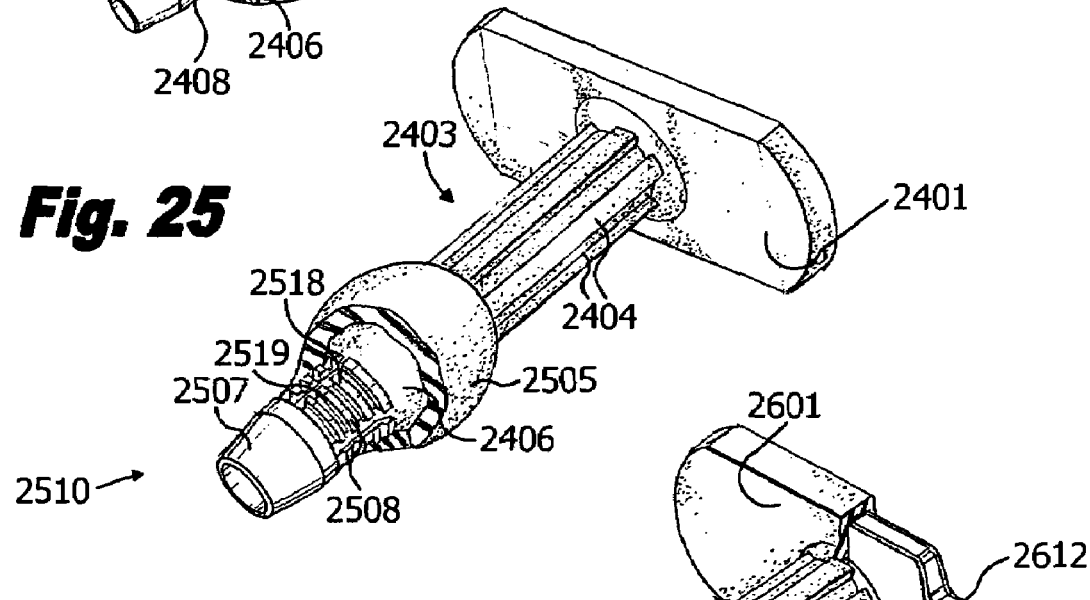
FIG. 25 is an isometric view of an additional embodiment of an access port in accordance with the invention, having a tip with flexible anchor elements provided thereon, for securing the tip to the access port body, and optionally for guiding surgical instruments through the lumen of the access port.
Figure 26:
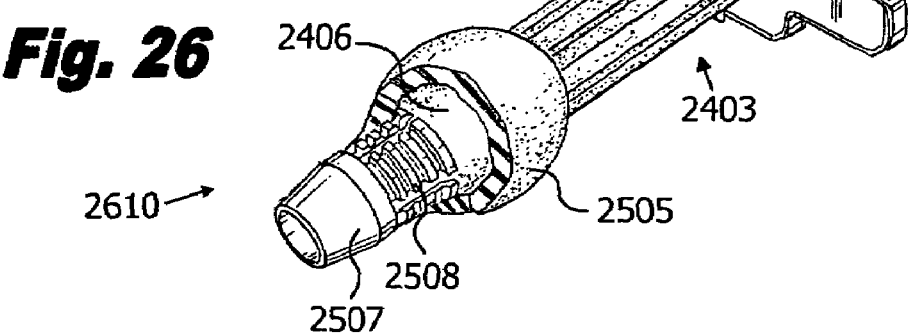
FIG. 26 is an isometric view of still another embodiment of an access port in accordance with the invention, having a flange reinforcing element provided thereon.
Figure 27:
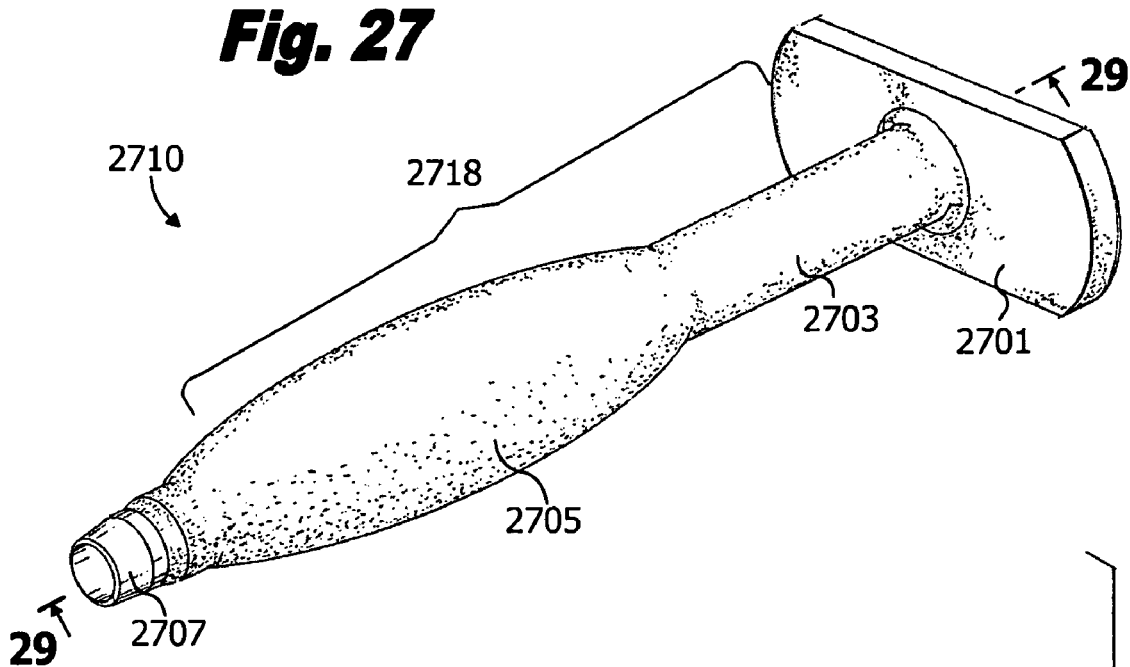
FIG. 27 is an isometric view of another embodiment of an access port in accordance with the invention, having a guide tube, valve and flange reinforcing element.
Figure 28:
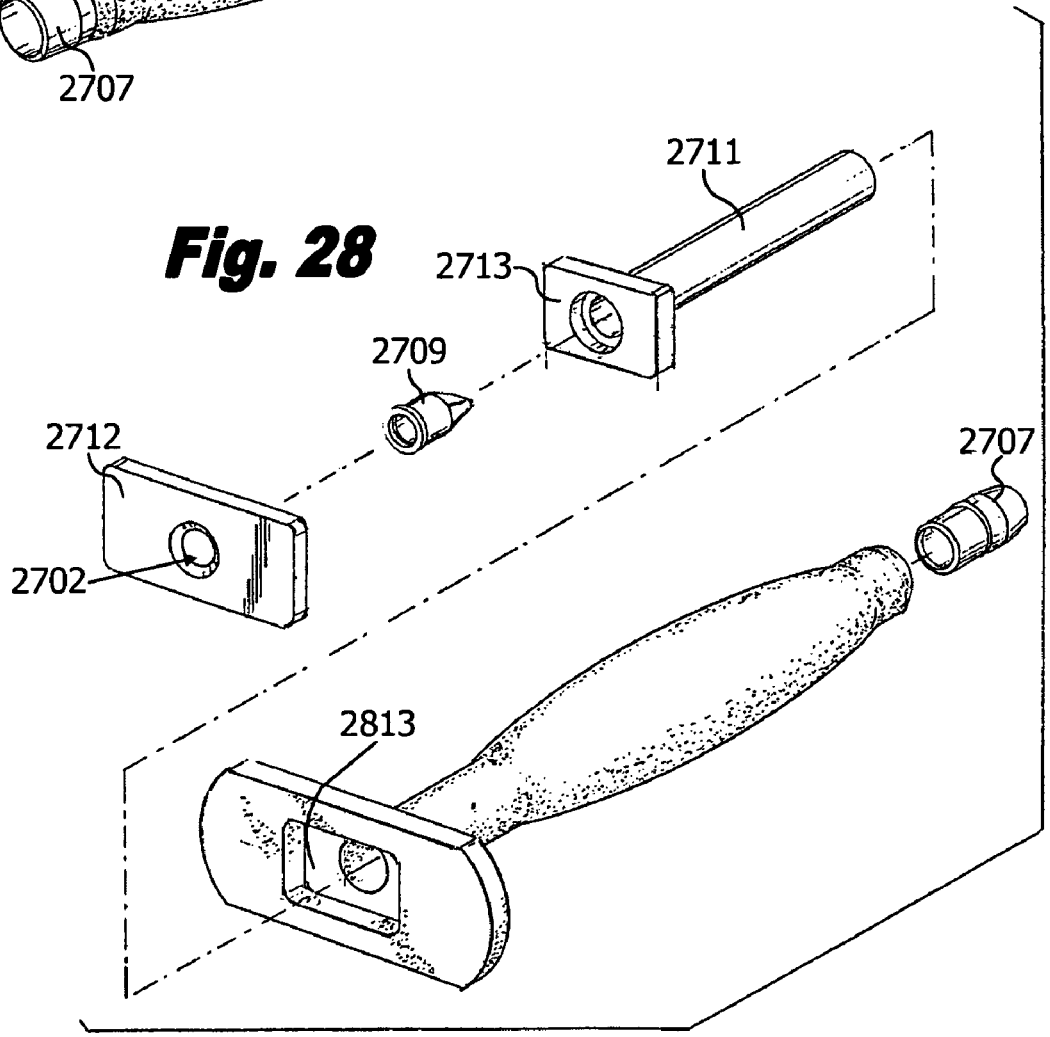
FIG. 28 is an exploded view of the access port of FIG. 27.

FIGS. 24-26 illustrate further embodiments of access ports 2410, 2510 and 2610 in accordance with the invention, each of which includes an extended neck portion 2403. The extended neck portion 2403 can be particularly advantageous when the access ports 2410, 2510 and 2610 are used in a patient having a relatively thick layer of abdominal fat, or an otherwise thick abdominal wall. The access port 2410 of FIG. 24 is substantially similar to many of the foregoing embodiments, with the exception of the elongated neck portion 2403. A proximal flange 2401 is connected to the elongated neck 2403, which in-turn includes longitudinal ribs 2404. The bulb 2405 extends from the neck portion 2403 and terminates in the distal tip 2407, which is connected thereto via extensions 2408.

The access port 2510 of FIG. 25 differs from that of FIG. 24, in the connection between the tip 2507 and the bulb portion 2505. While the construction of the flange 2401, neck portion 2403, and ribs 2404 is identical to that of the access port 2410 of FIG. 24, the tip 2507 includes anchor elements 2508, which extend into and are at least partially embedded into the material of the bulb 2505. The anchor elements 2508 include a longitudinal, inwardly oriented spine 2519 and one or more transverse protrusions 2518, which are embedded into the wall of the bulb 2505. The spine 2519, if desired, can be embedded within the bulb 2505, or can be arranged such that it is exposed to the lumen 2406 of the access port to aid passage of surgical instruments through the access port 2510.

The access port 2610 of FIG. 26 includes a configuration having an identical bulb 2505, tip 2507 and anchor elements 2508 to those of the embodiment of FIG. 25. Similarly, the neck 2403 is identical to each of the embodiments of FIGS. 24 and 25. The access port 2610 of FIG. 26 includes a rigid flange reinforcement 2612 arranged at the proximal end of the access port 2610. The flange reinforcement 2612 is provided, and in this case, recessed into the flange 2601 to impart increased rigidity to the flange 2601. While the flange 2601 can be integrally formed, e.g., molded, with the neck 2403 and bulb 2505 without such reinforcement 2612, such material may be undesirably soft to alone provide adequate rigidity for the flange 2601, because the flange 2601 must be pulled by a user when preparing the access port 2610 for insertion.

FIGS. 27-31 illustrate an access port 2710 in accordance with the invention composed of a plurality of components. As with the access port 1710 of FIGS. 17-19, the access port 2710 includes a guide tube 2711, a valve 2709, and a body 2718, which in-turn includes a flange 2701, neck 2703, bulb 2705, and terminates in a tip 2707. The valve 2709 resides within the guide tube 2711, which in-turn is inserted into the body 2718 of the access port 2710. A proximal flange 2713 of the guide tube 2711 is received by a recess 2813 defined in the flange 2701 of the access port body 2718.

Figure 29:
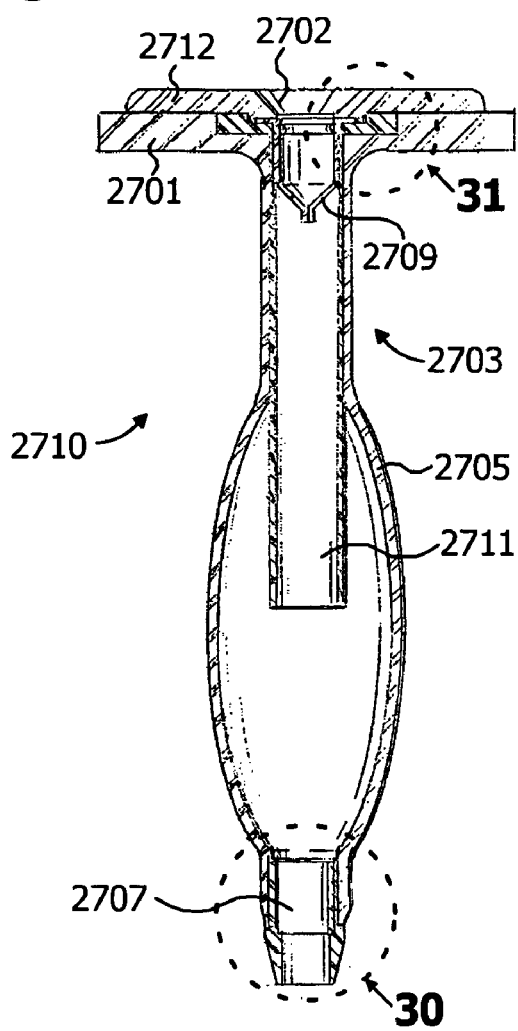
FIG. 29 is a cross-sectional view of the access port of FIG. 27, shown in a non-elongated configuration taken along line 29-29 thereof.
Figure 32:
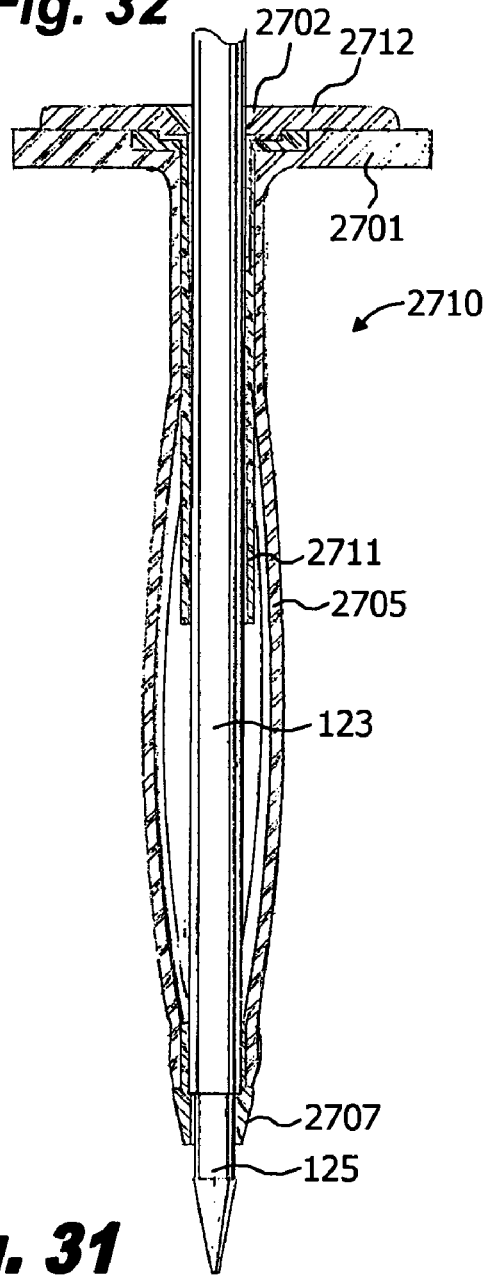
FIG. 32 is a cross-sectional view of the access port of FIG. 27, shown in an elongated configuration with an insertion device inserted in the access port.
Figure 30:
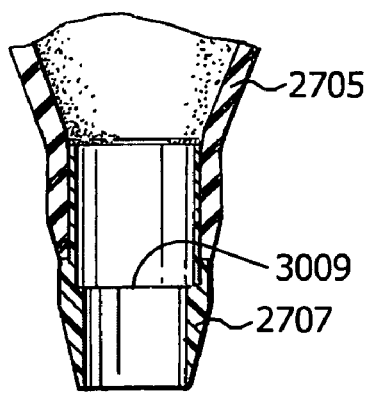
FIG. 30 is a detail view of region 30 in FIG. 29.
Figure 31:
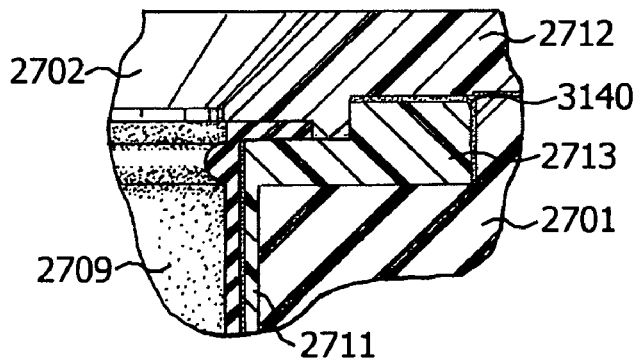
FIG. 31 is a detail view of region 31 in FIG. 29.

The access port 2710 additionally includes a flange reinforcement 2712, having a lead in surface 2702 to help guide insertion of surgical instruments. As with the access port 2610 of FIG. 26, the flange reinforcement 2712 imparts additional rigidity to the flange 2701. The flange reinforcement 2712 can be applied to the proximal surface of the flange 2701, or partially or fully recessed therein, as in the access port 2610 of FIG. 26. The individual components can be mutually secured by way of any suitable means, including, but not limited to heat welding, ultrasonic welding, solvent welding, adhesive, cohesive or, if desired, mechanical interlocking features. FIG. 31, which is a detail view of the respective portion of FIG. 29, illustrates an intermediate bonding material 3140, which can be an adhesive, for example. In a preferred embodiment, the bonding material 3140 is a material that melts upon application of heat energy, thereby mutually bonding the components of the access port 2710. As best seen in FIG. 30, which is a detail view of the respective region of FIG. 29, the tip 2707 includes an interior step 3009, which engages a mating component on the tip 125 of the insertion device (e.g., see FIG. 32). As can be seen, FIG. 29 illustrates the access port 2710 in a first configuration, prior to insertion through the abdominal wall, and FIG. 32 illustrates the access port 2710 in a second configuration, prepared for insertion through the abdominal wall of the patient.

Figure 33:
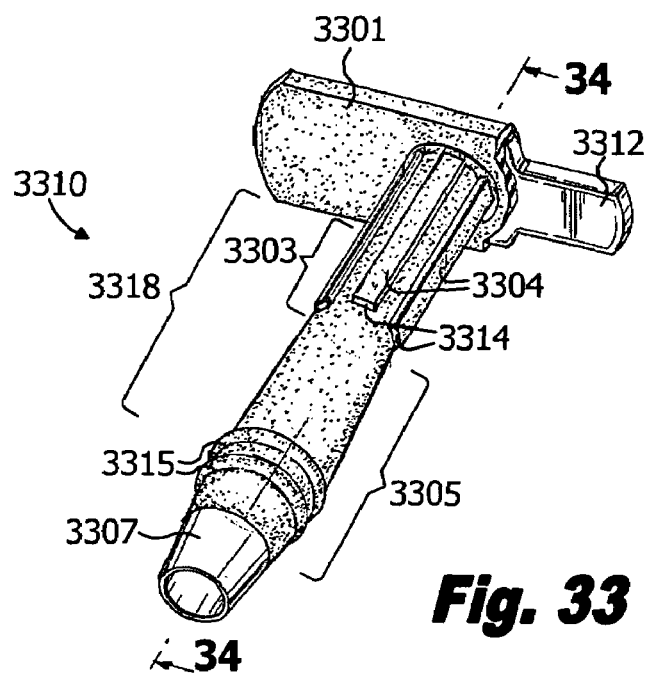
FIG. 33 is an isometric view of a further embodiment of an access port in accordance with the invention, having a generally flared configuration in the distal end portion thereof and circumferential ribs arranged thereon.

FIG. 33 is an isometric view of a further embodiment of an access port 3310 in accordance with the invention, having a generally flared configuration in the distal end portion of the body 3318. The flared region constitutes a bulb 3305, in that the expanded diameter of this region generally resembles such a configuration, and acts to anchor the access port 3310 in the abdominal wall of the patient. The access port 3310 includes a proximal flange 3301, with a flange reinforcing element 3312 arranged thereon, and a distal tip 3307 connected by the body 3318. Longitudinal ribs 3304 are formed on the neck portion 3303, and include a distal taper 3314 so that the ribs gradually approach the contour of the bulb portion 3305, as the diameter of the body 3318 increases toward the distal end of the access port 3310. Circumferential ribs 3315 further increase the diameter of the bulb portion 3305, providing additional anchoring capability. While the foregoing embodiments can be made from elastomeric materials or non-elastomeric materials, this embodiment preferably includes a material having a predetermined degree of elasticity, particularly because the relative diameter of the bulb portion 3305 to the remainder of the body 3318 of the access port 3310 is not as great as in many of the foregoing embodiments. Accordingly, when elongated, the material of the access port 3310 will stretch, and while the bulb 3305 decreases in profile, the ribs 3315, which are part of the bulb 3305, will also stretch longitudinally, effecting a reduction in their cross-sectional profile.

Figure 34:
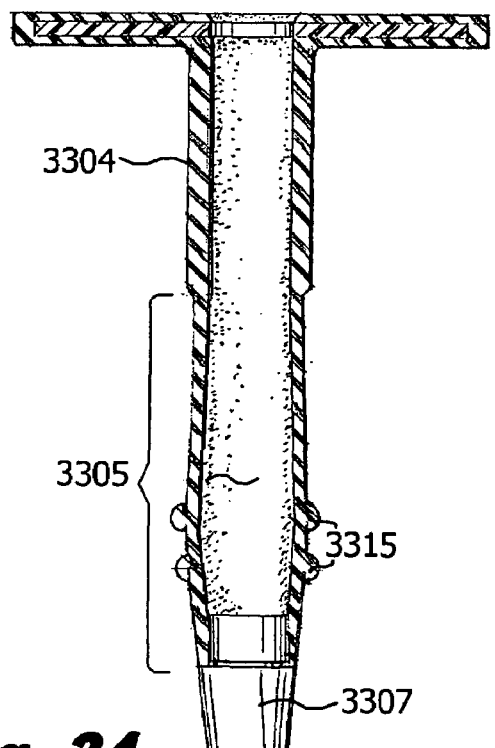
FIG. 34 is a partial cross-sectional view of the access port of FIG. 33.
Figure 35:
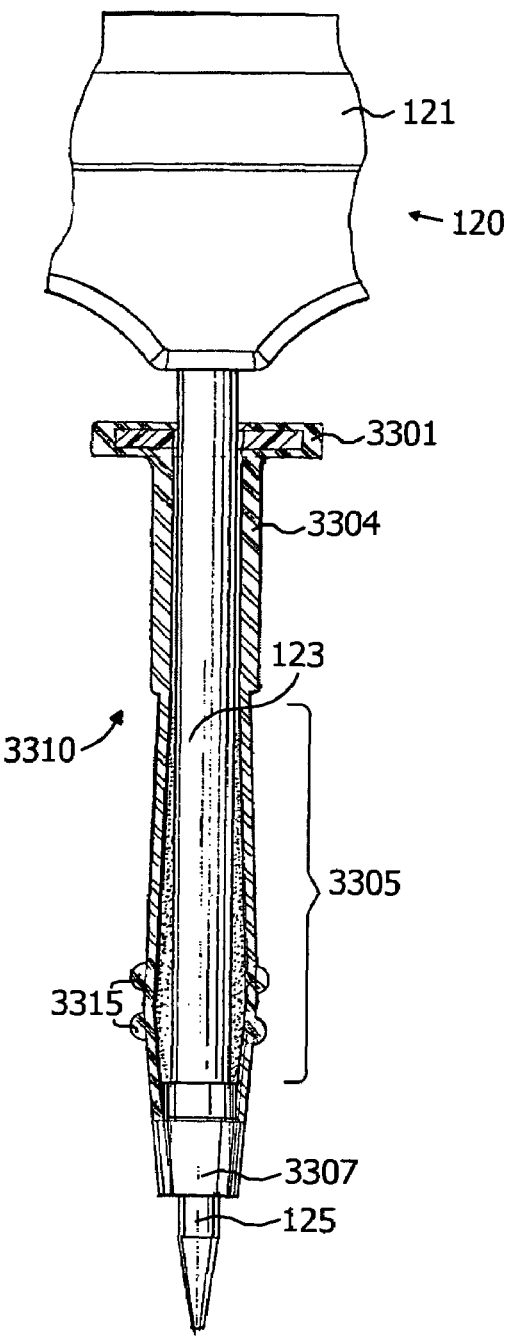
FIG. 35 is a partial cross-sectional view of the access port of FIG. 33, shown in an elongated configuration with an insertion device inserted in the access port.

FIG. 34 is a partial cross-sectional view of the access port of FIG. 33 and FIG. 35 is a partial cross-sectional view of the access port 3310 of FIG. 33, shown in an elongated configuration with an insertion device 120 inserted in the access port.

Figure 36:
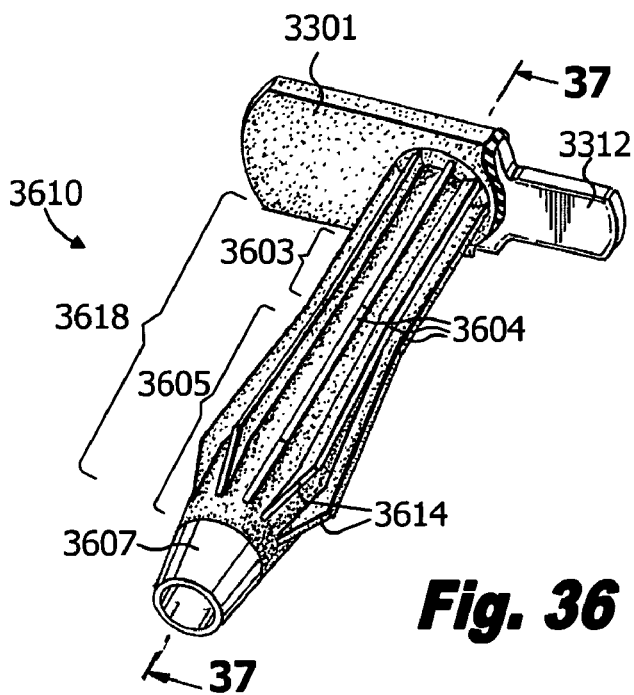
FIG. 36 is an isometric view of yet another access port in accordance with the invention, having a generally flared configuration in the distal end portion thereof with longitudinal ribs extending the length of the body thereof.

FIG. 36 is an isometric view of a further embodiment of an access port 3610 in accordance with the invention, also having a generally flared configuration in the distal end portion of the body 3618. The flared region constitutes a bulb 3605, which serves to anchor the access port 3610 in the abdominal wall of the patient. The access port 3610 includes a proximal flange 3301, with a flange reinforcing element 3312 arranged thereon, and a distal tip 3607, joined via the body 3618, as with the foregoing embodiment of FIG. 33. Longitudinal ribs 3604 are formed on the body 3618, which extend along the length thereof including along the neck portion 3603 thereof. The ribs 3604 include an increased height portion 3614 toward the distal end thereof, superimposed at an increased diameter portion of the body 3618. This embodiment also preferably includes a material having at least some degree of elasticity. Accordingly, when elongated, the material of the access port 3610 will stretch, with the bulb 3605 and ribs 3604 decreasing in profile.

Figure 37:
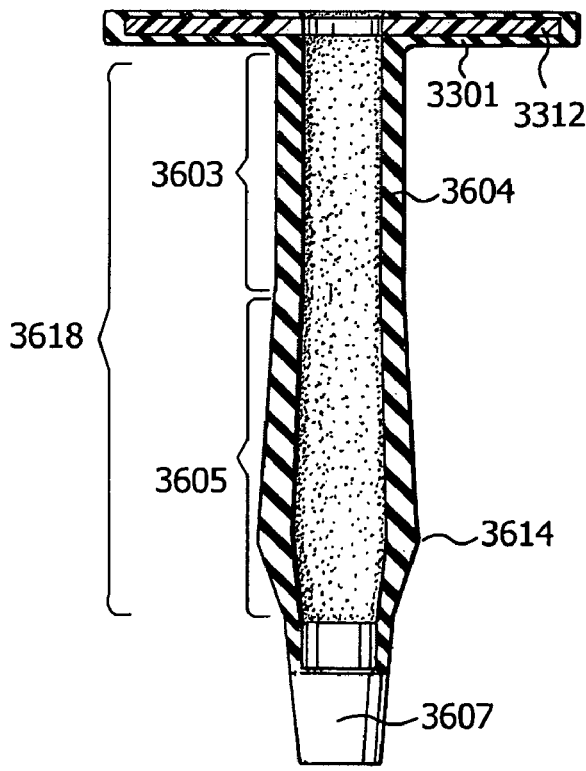
FIG. 37 is a partial cross-sectional view of the access port of FIG. 36 taken along line 37-37 thereof.
Figure 38:
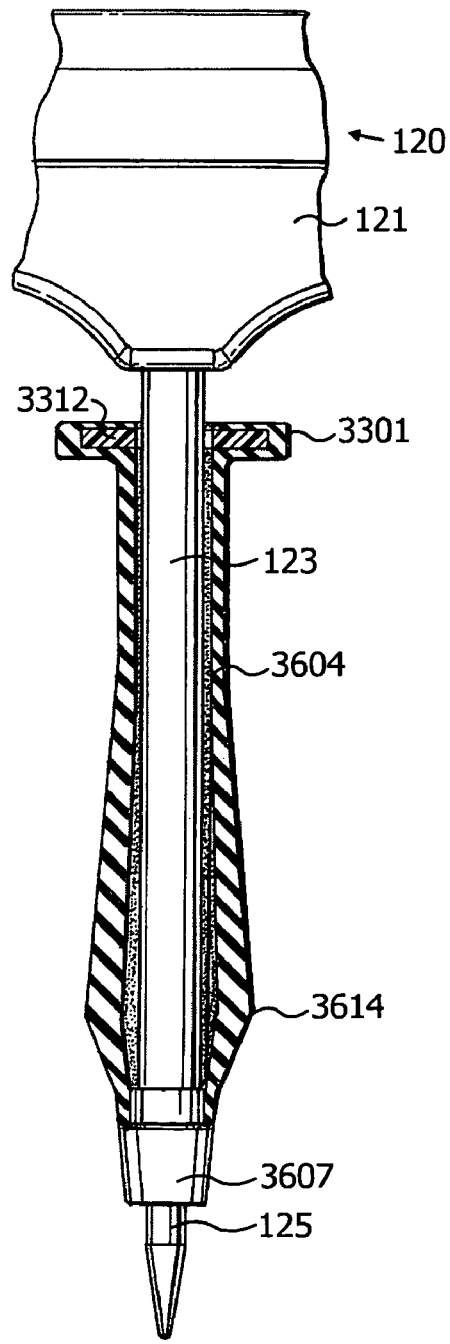
FIG. 38 is a partial cross-sectional view of the access port of FIG. 36, shown in an elongated configuration with an insertion device inserted in the access port.
Figure 44:
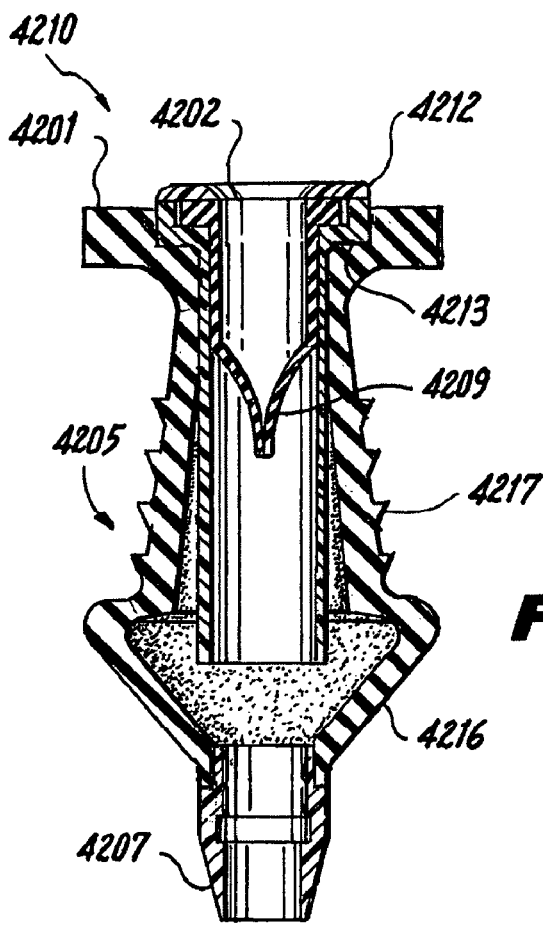
FIG. 44 is a side cross-sectional view of the access port of FIG. 42, illustrating in hidden line the arrangement of internal components thereof, taken across line 44-44 thereof.
Figure 45:
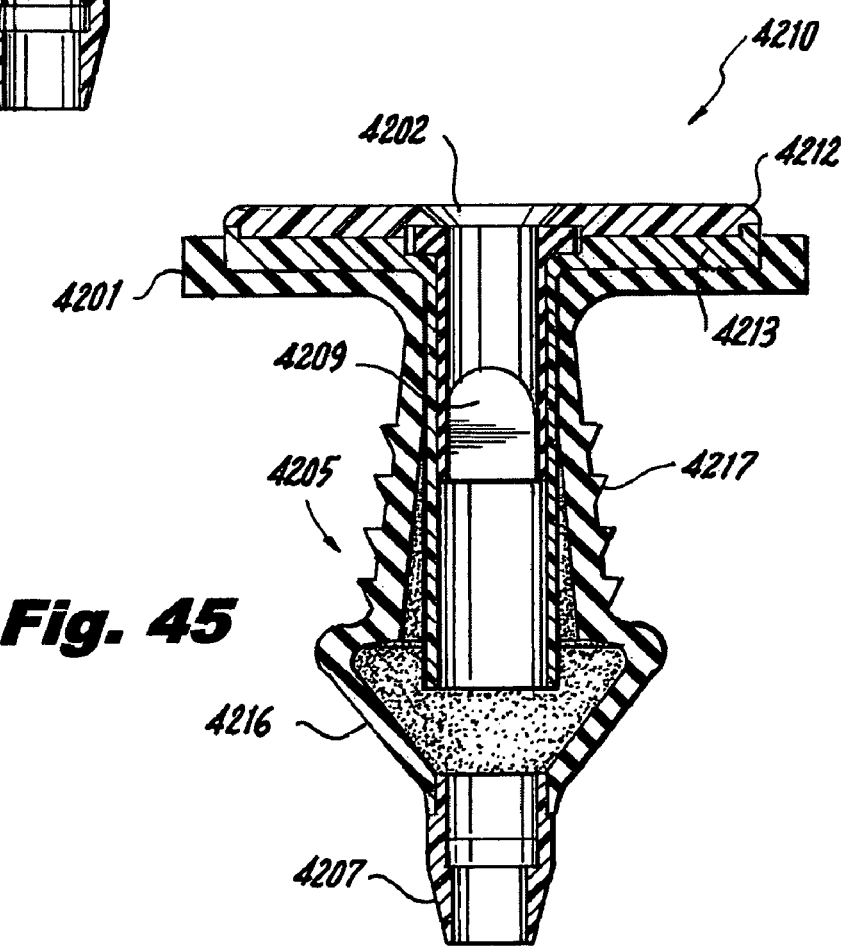
FIG. 45 is a front cross-sectional view of the access port of FIG. 42, also illustrating in hidden line the arrangement of internal components thereof, taken across line 45-45 thereof.

FIG. 37 is a partial cross-sectional view of the access port of FIG. 36 and FIG. 38 is a partial cross-sectional view of the access port of FIG. 36, shown in an elongated configuration with an insertion device 120 inserted in the access port 3610.

FIG. 39 is an isometric view of still another access port 3910 constructed in accordance with the invention, having longitudinal ribs 3904 in a neck portion 3903 and circumferential ribs 3915 in the distal bulb portion 3905 thereof. A tip 3907 is also provided, which is connected to the flange 3301 and reinforcing member 3312 by the body 3918 of the access port 3910. The ribs 3904 in the neck portion 3903 serve the purpose of preventing excessive elongation of the neck portion, when preparing the access port 3910 for insertion. The circumferential ribs 3915 in the bulb portion 3905 serve to resist unintended pullout of the access port 3910 from the abdominal wall of the patient. Therefore, it should be noted that as used herein, the term "bulb" refers to a region of expanded diameter, but which does not necessarily resemble a "bulb" shape. Accordingly, when elongated, the material of the access port 3910 will stretch, and while the bulb 3905 decreases in profile, the ribs 3915, which are part of the bulb portion 3905, will also stretch longitudinally, effecting a reduction in their cross-sectional profile, thereby facilitating insertion of the access port 3910 into the abdominal wall of the patient.

FIG. 40 is a partial cross-sectional view of the access port 3910 of FIG. 39, and FIG. 41 is a partial cross-sectional view of the access port 3910 of FIG. 39, shown in an elongated configuration with an insertion device 120 inserted in the access port.

FIGS. 42-45 illustrate an access port 4210 in accordance with the invention composed of a plurality of components, similar to the access port 2710 of FIGS. 27-31. The access port 4210 includes a guide tube 4211, a valve 4209, and a body 4218, which in-turn includes a flange 4201, neck 4203, bulb 4205, and terminates in a tip 4207. The valve 4209 resides within the guide tube 4211, which in-turn resides in the body 4218 of the access port 4210. A proximal flange 4213 (FIGS. 43-45) of the guide tube 4211 resides in a recess defined in the flange 4201 of the access port 4210.

The access port 4210 further includes a flange reinforcement 4212, having a lead in surface 4202 to help guide insertion of surgical instruments therethrough. As with other access ports set forth herein, the flange reinforcement 4212 helps impart rigidity to the flange 4201. The flange reinforcement 4212 can be applied to the proximal surface of the flange 4201, or partially or fully recessed therein.

In this embodiment, as best seen in the exploded view of FIG. 43, for example, the proximal flange 4213 of the guide tube 4211 is relatively large, and in combination with the enlarged flange reinforcement 4212, secures the valve 4209 to the body 4218 of the access port 4210 by engaging the valve 4209 therebetween.

As also can be seen in FIGS. 42-45, the bulb 4205 includes a single distal enlarged portion 4216, having an angled, generally barbed shape, and a plurality of ribs 4217 arranged along the length of the body 4218, which also have a generally barbed shape. Such shape, due to the angled contours thereof, enables relatively easy insertion, while still resisting pullout of the access port 4210 from the patient's abdominal wall.

As with foregoing embodiments, the individual components of the access port 4210 can be mutually secured by way of any suitable means, including, but not limited to heat welding, ultrasonic welding, solvent welding, adhesive, cohesive or, if desired, mechanical interlocking elements.

In order to remove an access port in accordance with the invention from the body of a patient, one can pull the proximal flange (e.g., flange 101 of FIG. 8) away from the abdominal wall. The counteracting force exerted by the abdominal wall will cause the surgical access port, and particularly the bulb portion (e.g., bulb 105 of FIG. 8) to elongate for removal from the body cavity into which it was inserted. Alternatively, in order to remove the port, the insertion device, or a similar blunt-tipped tool for engaging the distal end portion of the access port, can be inserted into the access port to elongate the access port for removal. The latter method, however, may be preferred in order to minimize trauma to the abdominal wall of the patient.

Surgical access devices in accordance with the invention can serve many purposes, only one of which is use in minimally-invasive surgical procedures. It should be appreciated by those skilled in the art, that access ports in accordance with the invention can be used wherever access, particularly sealable access, into a body cavity is needed.

The specific dimensions of surgical access devices, including access ports, in accordance with the invention can be selected as needed. Specifically, it is envisioned that a wide variety of sizes will be available to a user to enable the user to select the most appropriately dimensioned device for the patient and procedure at hand. The overall length of access ports in accordance with the invention can vary, as well as the relative lengths of the neck portions, diameters and lengths of bulb portions, dimensions of the flange dimensions of the access port, and the like. It is envisioned that the access ports set forth herein can replace typical rigid cannulas. Accordingly, general dimensions similar to such typical rigid cannulas are possible, although an operative (during surgery) length of the surgical access port, which is less than that of typical cannulas, is preferable.

Materials for access ports in accordance with the invention can include, as set forth above, plastics, composites, elastomers or metals if necessary, for any component or components thereof. For example, the flange and or tip can be reinforced by rigid plastic or metal components. As set forth above, materials having directional properties may be desirable.

The devices and methods of the present invention, as described above and shown in the drawings, provide for a surgical access device with superior properties including secure anchoring to the abdominal wall, low manufacture costs, and sealable access to a pneumoperitoneum. It will be apparent to those skilled in the art that various modifications and variations can be made in the device and method of the present invention without departing from the spirit or scope of the invention. For example, an insufflation port can be incorporated into the subject surgical access port, if desired. Thus, it is intended that the present invention include modifications and variations that are within the scope of the appended claims and their equivalents.

What is claimed is:

1. A surgical access device comprising:
   (a) an access port adapted and configured for insertion through an abdominal wall of a patient and to permit insertion and removal of surgical instruments therethrough, the access port having an elongated body with opposed proximal and distal end portions and defining a longitudinal axis, the body having a central lumen extending therethrough and having a resilient bulb portion formed between the proximal and distal end portions thereof, at a position on the body permitting engagement of the bulb portion with an interior surface of the abdominal wall, wherein the resilient bulb portion is adapted and configured to transition between a first condition in which the bulb portion has a first diameter and a first length and a second condition in which the bulb portion has a second diameter that is less than the first diameter and a second length that is greater than the first length;
   (b) a tip secured to and extending beyond the distal end portion of the access port, wherein the central lumen extends through the tip; and
   (c) an elongated insertion device adapted to extend into the central lumen of the access port body and into the central lumen of the tip, wherein the insertion device is configured to releasably engage the tip so as to facilitate a transition from the first condition of the bulb portion of the access port body to the second condition of the bulb portion of the access port body.

2. A surgical access device as recited in claim 1, wherein the bulb portion has a generally spherical configuration in the first condition.

3. A surgical access device as recited in claim 1, wherein the bulb portion has a generally ovoid configuration in the first condition.

4. A surgical access device as recited in claim 1, wherein the tip includes an insert sleeve disposed within the distal end portion of the access port body for engaging a distal end portion of the insertion device.

5. A surgical access device as recited in claim 4, wherein the insert sleeve is formed from a material having a greater rigidity than the access port body.

6. A surgical access device as recited in claim 5, wherein the insert sleeve includes a plurality of proximally extending expandable guide fingers for lining an inner surface of the bulb portion to accommodate insertion of the insertion device.

7. A surgical access device as recited in claim 1, further comprising a substantially rigid generally planar flange portion associated with the proximal end portion of the access port body and defining a proximal access opening communicating with the lumen of the access port body.

8. A surgical access device as recited in claim 7, wherein the access port has a conically tapering lead-in surface.

9. A surgical access device as recited in claim 7, wherein the insertion device includes a handle with releasable locking means for releasably engaging the flange portion at the proximal end portion of the access port body.

10. A surgical access device as recited in claim 1, wherein the proximal end portion of the access port body has a substantially constant outer diameter.

11. A surgical access device as recited in claim 10, wherein the proximal portion of the access port body is provided with longitudinal, circumferentially spaced ribs formed on an outer surface of the body, for inhibiting elongation of the proximal end portion of the access port body during the transition from the first condition of the bulb portion to the second condition of the bulb portion.

12. A surgical access device as recited in claim 1, wherein the body is provided with circumferential, longitudinally spaced ribs formed on an outer surface of the body, for inhibiting removal of the bulb portion from an abdominal wall of a patient.

13. A surgical access device as recited in claim 1, wherein a seal member is disposed within the lumen in the proximal end portion of the access port body.

14. A surgical access device as recited in claim 1, wherein a seal is integrally formed within the lumen in the proximal end portion of the access port body.

15. A surgical access device as recited in claim 1, further comprising a seal region defined in the proximal end portion of the body such that the seal region can be compressed or collapsed by an outside force, to seal the lumen.

16. A surgical access device as recited in claim 15, wherein the seal region is defined in an elongate neck portion formed in the body.

17. A surgical access device as recited in claim 15, wherein the seal region is generally ovoid in cross-sectional configuration.

18. A surgical access device as recited in claim 1, further comprising an elongated guide tube attached to the proximal end portion of the access port body that extends through the proximal portion of the access port body and at least partially into the bulb portion of the access port body, wherein the guide tube and bulb cooperate to define an annular space along a substantial portion of the bulb portion of the access port body when the access port body is in the first condition.

19. A surgical access device as recited in claim 1, wherein at least the bulb portion of the access port body is formed at least in part from an elastomeric material.

20. A surgical access device as recited in claim 1, wherein at least the bulb portion of the access port body is formed at least in part from silicone rubber.

21. A surgical access device as recited in claim 1, wherein the bulb portion, in the first condition, has an outer surface with a substantially convex arcuate contour that is continuous about the circumference of the bulb portion.

22. A surgical access device as recited in claim 1, wherein the bulb portion in the first condition includes an expanded diameter.

23. A surgical access device as recited in claim 1, wherein the tip is provided with a first engagement means in the distal end portion thereof, a distal end portion of the insertion device engaging the first engagement means.

24. A surgical access device as recited in claim 23, wherein the first engagement means is a substantially rigid stepped element, for engaging a mating portion of the insertion device.

25. A surgical access device as recited in claim 23, the body being provided with second engagement means in the proximal end portion thereof, a proximal end of the insertion device engaging the second engagement means, the insertion device having a length greater than the first length of the bulb portion of the body, causing extension of the bulb portion to the second length thereof.

26. A surgical access device as recited in claim 1, further comprising a duckbill valve configured within the lumen of the access port, capable of inhibiting proximally directed fluid flow.

27. A surgical access device as recited in claim 1, further comprising a ball valve provided within the lumen of the access port, capable of inhibiting proximally directed fluid flow.

28. A surgical access device comprising:
(a) an access port adapted and configured for insertion through an abdominal wall of a patient and to permit insertion and removal of surgical instruments therethrough, the access port having an elongated body with opposed proximal and distal end portions and defining a longitudinal axis, the body having a central lumen extending therethrough and having a resilient bulb portion formed between the proximal and distal end portions thereof, at a position on the body permitting engagement of the bulb portion with an interior surface of the abdominal wall, wherein the resilient bulb portion is adapted and configured to transition between a first condition in which the bulb portion has a first diameter and a first length and a second condition in which the bulb portion has a second diameter that is less than the first diameter and a second length that is greater than the first length;
(b) a first engagement means arranged in the distal end portion of the access port body;
(c) an elongated guide tube attached to the proximal end portion of the access port body that extends through the proximal portion of the access port body and into the bulb portion, wherein the guide tube and bulb cooperate to define an annular space along a substantial portion of the bulb portion of the access port body when the access port body is in the first condition; and
(d) an insertion device adapted and configured to releasably engage the first engagement means so as to facilitate a transition from the first condition of the bulb portion of the access port body to the second condition of the bulb portion of the access port body.

29. A surgical access device as recited in claim 28, further comprising a second engagement means arranged in the proximal end portion of the body, for engagement with a proximal end portion of the insertion device, the insertion device maintaining the access port body in the second condition while engaged with the first and second engagement means.

30. A method of forming an access port in a patient, the method comprising the steps of:
(a) providing an access port adapted and configured for insertion through an abdominal wall of a patient and to permit insertion and removal of surgical instruments therethrough, the access port having an elongated body with opposed proximal and distal end portions and defining a longitudinal axis, the body having a central lumen extending therethrough and having a resilient bulb portion formed between the proximal and distal end portions thereof, at a position on the body permitting engagement of the bulb portion with an interior surface of the abdominal wall, wherein the resilient bulb portion is adapted and configured to transition between a first condition in which the bulb portion has a first diameter and a first length and a second condition in which the bulb portion has a second diameter that is less than the first diameter and a second length that is greater than the first length, and wherein the access port further includes an elongated guide tube attached to the proximal end portion of the access port body that extends through the proximal portion of the access port body and into the bulb portion, wherein the guide tube and bulb portion cooperate to define an annular space along a substantial portion of the bulb portion of the access port body when the access port body is in the first condition;
(b) providing an insertion device configured to releasably engage the distal end portion of the access port body;
(c) extending the insertion device into the central lumen of the access port body so as to releasably engage the distal end portion of the access port body;
(d) elongating the access port with the insertion device to cause the annular space to collapse, the end of the insertion device being engaged with the distal end portion of the access port body;
(e) inserting the access port and insertion device through the abdominal wall to a predetermined position, while maintaining the access port in an elongated configuration; and
(f) removing the insertion device from the access port, allowing the access port to revert to the first configuration and permitting the annular space to expand, with the bulb portion of the access port engaging an interior surface of the abdominal wall.

31. A method as recited in claim 30, further comprising sealing the central lumen.

32. A method as recited in claim 31, wherein sealing occurs by a radially inwardly directed force acting on the access port, exerted by the abdominal wall of the patient.

33. A method as recited in claim 30, further comprising the step of performing surgery by inserting a surgical instrument through the lumen of the access port.

34. A method as recited in claim 30, further comprising sealing between the access port and the surgical instrument.

35. A method as recited in claim 34, wherein sealing occurs by a radially inwardly directed force acting on the access port, exerted by the abdominal wall of the patient.

36. A method as recited in claim 30, wherein the step of elongating the access port with the insertion device further comprises engaging the insertion device with a first engagement means at the distal end of the access port and elongating the port along the insertion device.

37. A method as recited in claim 36, further comprising the step of engaging a second engaging means associated with the proximal end of the access port with a corresponding engagement means on the insertion device to selectively maintain the access port body in an elongated configuration.

38. A method as recited in claim 37, wherein the step of inserting the port comprises inserting the access port through the abdominal wall with the insertion device in engagement with the first and second engagement means of the access port.

39. A method as recited in claim 38, further comprising removing the access port from the abdominal wall.

40. A method as recited in claim 30, further comprising removing the access port from the abdominal wall.

41. A method as recited in claim 40, wherein the step of removing the access port from the abdominal wall further comprises reengaging the insertion device with the first and second engagement means to elongate the access port body, and withdrawing the elongated access port from the abdominal wall.

* * * * *